United States Patent
Kudithipudi et al.

(10) Patent No.: US 12,291,715 B2
(45) Date of Patent: *May 6, 2025

(54) GENETIC LOCUS IMPARTING A LOW ANATABINE TRAIT IN TOBACCO AND METHODS OF USING

(71) Applicant: ALTRIA CLIENT SERVICES INC., Richmond, VA (US)

(72) Inventors: Chengalrayan Kudithipudi, Midlothian, VA (US); Alec J. Hayes, Chesterfield, VA (US); Robert Frank Hart, III, Midlothian, VA (US); Yanxin Shen, Glen Allen, VA (US); Jesse Frederick, Richmond, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/527,834

(22) Filed: Dec. 4, 2023

(65) Prior Publication Data

US 2024/0117371 A1    Apr. 11, 2024

Related U.S. Application Data

(63) Continuation of application No. 17/683,227, filed on Feb. 28, 2022, now Pat. No. 11,873,500, which is a continuation of application No. 16/825,394, filed on Mar. 20, 2020, now Pat. No. 11,299,743, which is a continuation of application No. 14/794,092, filed on Jul. 8, 2015, now Pat. No. 10,626,409.

(60) Provisional application No. 62/021,738, filed on Jul. 8, 2014.

(51) Int. Cl.
| | | |
|---|---|---|
| *C12N 15/82* | (2006.01) | |
| *A01H 1/04* | (2006.01) | |
| *A01H 1/06* | (2006.01) | |
| *A01H 5/12* | (2018.01) | |
| *A01H 6/82* | (2018.01) | |
| *A24B 13/00* | (2006.01) | |
| *C12Q 1/6895* | (2018.01) | |

(52) U.S. Cl.
CPC ......... *C12N 15/8261* (2013.01); *A01H 1/045* (2021.01); *A01H 1/06* (2013.01); *A01H 5/12* (2013.01); *A01H 6/823* (2018.05); *A24B 13/00* (2013.01); *C12N 15/8218* (2013.01); *C12N 15/8243* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh, Jr. et al. |
| 4,660,577 A | 4/1987 | Sensabaugh, Jr. et al. |
| 4,683,195 A | 7/1987 | Mullis et al. |
| 4,683,202 A | 7/1987 | Mullis et al. |
| 4,761,373 A | 8/1988 | Anderson et al. |
| 4,769,061 A | 9/1988 | Comai |
| 4,800,159 A | 1/1989 | Mullis et al. |
| 4,810,648 A | 3/1989 | Stalker |
| 4,848,373 A | 7/1989 | Lenkey |
| 4,940,835 A | 7/1990 | Shah et al. |
| 4,965,188 A | 10/1990 | Mullis et al. |
| 4,975,374 A | 12/1990 | Goodman et al. |
| 5,013,659 A | 5/1991 | Bedbrook et al. |
| 5,162,602 A | 11/1992 | Somers et al. |
| 5,164,180 A | 11/1992 | Payne et al. |
| 5,276,268 A | 1/1994 | Strauch et al. |
| 5,372,149 A | 12/1994 | Roth et al. |
| 5,545,565 A | 8/1996 | De Greve et al. |
| 5,561,236 A | 10/1996 | Leemans et al. |
| 5,767,366 A | 6/1998 | Sathasivan et al. |
| 5,879,903 A | 3/1999 | Strauch et al. |
| 5,928,937 A | 7/1999 | Kakefuda et al. |
| 6,084,155 A | 7/2000 | Volrath et al. |
| 6,166,302 A | 12/2000 | Merlo et al. |
| 6,451,732 B1 | 9/2002 | Beckett et al. |
| 6,451,735 B1 | 9/2002 | Ottaway et al. |
| 7,293,564 B2 | 11/2007 | Perfetti et al. |
| 2001/0016956 A1 | 8/2001 | Ward et al. |
| 2004/0118422 A1 | 6/2004 | Lundin et al. |
| 2005/0178398 A1 | 8/2005 | Breslin et al. |
| 2005/0244521 A1 | 11/2005 | Strickland et al. |
| 2006/0191548 A1 | 8/2006 | Strickland et al. |

(Continued)

FOREIGN PATENT DOCUMENTS

| | | |
|---|---|---|
| EP | 0 242 246 B1 | 11/1992 |
| EP | 2 537 929 A1 | 12/2012 |
| WO | WO 06/109197 A2 | 10/2006 |

OTHER PUBLICATIONS

Schiavinato, Matteo, et al. "Parental origin of the allotetraploid tobacco Nicotiana benthamiana." The Plant Journal 102.3 (2020):541-554. (Year: 2020).*

(Continued)

*Primary Examiner* — Weihua Fan

(74) *Attorney, Agent, or Firm* — Arnold & Porter Kaye Scholer LLP

(57) ABSTRACT

Provided herein are genetic markers and a coding sequence associated with a low- or ultra-low anatabine trait in tobacco.

18 Claims, 9 Drawing Sheets

Specification includes a Sequence Listing.

(56) References Cited

U.S. PATENT DOCUMENTS

| | | | |
|---|---|---|---|
| 2007/0240728 A1* | 10/2007 | Hashimoto | A24B 15/243 800/278 |
| 2012/0024301 A1 | 2/2012 | Carroll et al. | |
| 2012/0031414 A1 | 2/2012 | Atchley et al. | |
| 2012/0031416 A1 | 2/2012 | Atchley et al. | |
| 2013/0056014 A1* | 3/2013 | Noguchi | C12N 15/8279 800/278 |
| 2015/0322451 A1 | 11/2015 | Kudithipudi et al. | |

OTHER PUBLICATIONS

Nekrasov, Vladimir, et al. "Targeted mutagenesis in the model plant Nicotiana benthamiana using Cas9 RNA-guided endonuclease." Nature biotechnology 31.8 (2013): 691-693. (Year: 2013).*

Chenna et al., "Multiple sequence alignment with the Clustal series of programs," Nucleic Acids Research, 31(13): 3497-3500 (2003).

Dayhoff et al., "22 A Model of Evolutinoalry Change in Proteins," Atlas of Protein Sequence and Structure, vol. 5, Suppl. 3, pp: 345-352, Natl Biomed Res Found (1978) (Washington).

DeBoer et al., "RNAi-mediated down-regulation of ornithine decarboxylase (ODC) leads to reduced nicotine and increased anatabine levels in transgenic *Nicotiana tabacum* L.," Phytochemistry, 72(4-5):344-355 (2011).

Dewey et al., "Molecular genetics of alkaloid biosynthesis in Nicotiana tabacum," Phytochemistry, 94:10-27 (2013).

"Draft for Diplomatic Conference for The Revision of The International Convention for The Protection of New Varieties of Plants," Mar. 4-9, 1991 (Geneva, Zwitcherland).

Esakova et al., "Structure of Quinolinate Synthase from *Pyrococcus horikoshii* in the Presence of is Product, Quinolinic Acid," *J. Am. Chem. Soc.*, 138(23):7224-7227 (2016).

Fischhoff et al., "Insect Tolerant Transgenic Tomato Plants," *Nature BioTechnology*, 5:807-813 (1987).

Hibi et al., "Gene Expression in Tobacco Low-Nicotine Mutants," Plant Cell. May 1994;6(5):723-35.

International Preliminary Report on Patentability dated Jan. 10, 2017, in International Application No. PCT/US2015/039562, 7 pgs.

International Search Report and Written Opinion dated Oct. 29, 2015, in International Application No. PCT/US2015/039562, 13 pgs.

Li et al., "Modularly assembled designer TAL effector nucleases for targeted gene knockout and gene replacement in eukaryotes," *Nucleic Acids Research*, 39(14): 6315-6325 (2011).

Nekrasov et al., "Targeted mutagenesis in the model plant *Nicotiana benthamiana* using Cas9 RNA-guided endonuclease," *Nature biotechnology*, 31(8):691-693 (2013).

Ollagnier-de Choudens et al., "Quinolinate synthetase, an iron-sulfur enzyme in NAD biosynthesis," *FEBS Letters*, 579:3737-3743 (2005).

Punta et al., "The Pfam protein families database," *Nucleic Acids Research*, 40:D290-D301 (2012).

Schiavinato, et al. "Parental origin of the allotetraploid tobacco Nicotiana benthamiana." *The Plant Journal* 102.3 (2020): 541-554. (Year: 2020).

Sisson et al., "Alkaloid composition of the *Nicotiana* species," *Beitrage zur Tabakforschung International* 14.6:327-339 (1990).

Sun et al., "Genetic variation in alkaloid accumulation in leaves of Nicotiana," *J Zhejiang Univ Sci B.*, 14(12):1100-1109 (2013).

Sun et al., "An extended set of yeast-based functional assays accurately identifies human disease mutations," *Genome Research*, 26(5):670-680 (2016).

Timko, "Science Based Approaches for the Production and Evaluation of Modified Risk Tobacco Products," 96th Annual Tobacco Manufacturer's Association Conference Evidence-Based Science and Regulation of the Tobacco Industry Williamsburg VA, pp. 1-20 (2011) <http://www.tma.ore/tmalive/Html/Advertisements/Timko.pdf>.

Vaeck et al., "Transgenic plants protected from insect attack," *Nature*, 328:33-37 (1987).

Wang et al., "Silencing of PMT expression caused a surge of anatabine accumulation in tobacco," *Mol Biol Rep*, 36(8):2285-2289 (2009).

Weeks et al., "Use of designer nucleases for targeted gene and genome editing in plants," *Plant Biotechnol. J.*, 14:483-495 (2016).

Wei et al., "Testing computational prediction of missense mutation phenotypes: Functional characterization of 204 mutations of human cystathionine beta synthase," *Proteins: Structure, Function, and Bioinformatics*, 78(9):2058-2074 (2010).

Wright et al., "High-frequency homologous recombination in plants mediated by zinc-finger nucleases," *The Plant Journal*, 44:693-705 (2005).

Yoo et al., "*Arabidopsis* medophyll protoplasts: a versatile cell system for transient gene expression analysis," *Nature Protocols*, 2(7):1565-1572 (2007).

* cited by examiner

Panel B

```
                 1,448                              1,477
1. M207     AGGATGGGACA TG TATTGTTCATCACCTCT
             D  G  T  [X] I  V  H  H  L

2. M544     AGGATGGGACATGTATTGTTCATCACCTCT
             D  G  T  C  I  V  H  H  L

3. Fc401 WT AGGATGGGACATGTATTGTTCATCACCTCT
             D  G  T  C  I  V  H  H  L 1,536                          1,561
1. M207     CACACTTTGAAGTTCCTGGTGAAATG
             H  F  E  V  P  G  E  M

2. M544     CACACTTTGA G  TTCCTGGTGAAATG
             H  F  E  [ ]  P  G  E  M

3. Fc401 WT CACACTTTGAAATTCCTGGTGAAATG
             H  F  E  V  P  G  E  M
```

Figure 4

```
 1. Fc401 WT    GTCIVHHLFGHEVVENINEMYGDAFLTAHFEVPGEMFSLAM
 2. M207        GTYIVHHLFGHEVVENINEMYGDAFLTAHFEVPGEMFSLAM
 3. M544        GTCIVHHLFGHEVVENINEMYGDAFLTAHFEIPGEMFSLAM
 4. D5LAT9/169-49  GTCIVHHIFGGEVTELVAAGYGDAYLAAHFEVPGEMFRLAM
 5. D5LAX9/215-54  GTCIVHHIFGGEVTELVAAGYGDAYLAAHFEVPGEMFRLAM
 6. D7FHH3/111-39  GNCIVHHMFGDDVVERVRSNHADAFHTAHLEVPGEMFRLAM
 7. D7MPK3/260-66  GTCIVHHLFGHEVVERTKYMYCDAFITAHLEVPGEMFSLAM
 8. D7SHG8/133-45  GTCIVHHLFGHEVVEKTNEMYCDAFITAHLEVPGEMFSLAM
 9. D8QQE7/239-65  GSCIVHDMFGHDVVSRVREGYGDAYLTAHFEVPGEMFTLAM
10. D8R818/237-58  GSCIVHDMFGHDVVSRVREGYGDAYLTAHFEVPGEMFTLAM
11. D8U8Q3/237-49  GTCIVHHIFGGEVAELVRRAYGDAYLAAHFEVPGEMFGLAM
```

GENETIC LOCUS IMPARTING A LOW ANATABINE TRAIT IN TOBACCO AND METHODS OF USING

CROSS-REFERENCE TO RELATED APPLICATIONS

This application is a continuation of U.S. patent application Ser. No. 17/683,227, filed Feb. 28, 2022, which is continuation of U.S. patent application Ser. No. 16/825,394, filed Mar. 20, 2020, now U.S. Pat. No. 11,299,743, issued Apr. 12, 2022, which is a continuation of U.S. patent application Ser. No. 14/794,092, filed Jul. 8, 2015, now U.S. Pat. No. 10,626,409, issued Apr. 21, 2020, which claims the benefit of U.S. Provisional Application No. 62/021,738, filed Jul. 8, 2014, all of which are incorporated by reference in their entireties herein.

INCORPORATION OF SEQUENCE LISTING

A sequence listing contained in the file named "P34624US04.xml" which is 64,1396 bytes (measured in MS-Windows®) and created on Dec. 1, 2023, is filed electronically herewith and incorporated by reference in its entirety.

TECHNICAL FIELD

This disclosure relates to genetic markers and the coding sequence associated with the locus that imparts a low anatabine trait in tobacco.

BACKGROUND

Anatabine is a minor alkaloid in tobacco and it is also a precursor for N'-nitrosoanatabine (NAT), one of four tobacco-specific nitrosamines (TSNAs) found in cured tobacco. Even though anatabine constitutes only about 3% of the total alkaloids found in tobacco, NAT constitutes about 40%-50% of the total amount of TSNAs. Therefore, reducing the amount of anatabine in a tobacco plant may be a viable way to reduce the overall amount of TSNAs in cured tobacco.

SUMMARY

This disclosure describes a correlation between a low anatabine trait and the quinolinate synthase (QS) gene. The correlation is useful for understanding the alkaloid synthesis pathway and its regulation, particularly with respect to anatabine. Single nucleotide polymorphisms (SNPs) in the QS gene also provide markers for breeding the low anatabine or ultra-low anatabine (ULA) trait into tobacco lines.

In one aspect, a tobacco hybrid, variety, line, or cultivar is provided that includes plants having a mutation in an endogenous nucleic acid having the sequence shown in SEQ ID NO: 7. In some embodiments, the mutant plants exhibit reduced expression or activity of QS. In some embodiments, leaf from the mutant plants exhibit reduced amounts of at least one alkaloid (e.g., anatabine). In some embodiments, cured leaf from the mutant plants exhibit a reduced amount of at least one TSNA (e.g., N'-nitrosoanatabine (NAT)).

In another aspect, seed produced by any of the tobacco hybrids, varieties, lines, or cultivars described herein, the seed including the mutation in an endogenous nucleic acid having the sequence shown in SEQ ID NO: 7.

In still another aspect, a method of making a tobacco plant is provided. Such a method typically includes the steps of inducing mutagenesis in Nicotiana tabacum cells to produce mutagenized cells; obtaining one or more plants from the mutagenized cells; and identifying at least one of the plants that comprises a mutation in an endogenous nucleic acid having the sequence shown in SEQ ID NO: 7.

In some embodiments, such a method further includes identifying at least one of the plants that comprises leaf exhibiting a reduced amount of at least one alkaloid relative to leaf from a plant lacking the mutation. In some embodiments, the at least one alkaloid is anatabine. In some embodiments, the method further includes identifying at least one of the plants that comprises leaf that, when cured, exhibit a reduced amount of at least one TSNA relative to cured leaf from a plant lacking the mutation. In some embodiments, the at least one TSNA is NAT.

In some embodiments, mutagenesis is induced using a chemical mutagen or ionizing radiation. Representative chemical mutagens include, without limitation, nitrous acid, sodium azide, acridine orange, ethidium bromide, and ethyl methane sulfonate (EMS). Representative ionizing radiation includes, without limitation, x-rays, gamma rays, fast neutron irradiation, and UV irradiation. In some embodiments, mutagenesis is induced using TALEN. In some embodiments, mutagenesis is induced using zinc-finger technology.

In yet another aspect, a method for producing a tobacco plant is provided. Such a method typically includes the steps of: crossing at least one plant of a first tobacco line with at least one plant of a second tobacco line, the plant of the first tobacco line having a mutation in an endogenous nucleic acid having the sequence shown in SEQ ID NO: 7; and selecting for progeny tobacco plants that have the mutation.

In some embodiments, the method further includes selecting for progeny tobacco plants that comprise leaf exhibiting reduced expression or activity of QS relative to leaf from a plant lacking the mutation. In some embodiments, the method further includes selecting for progeny tobacco plants that comprise leaf exhibiting a reduced amount of at least one alkaloid relative to leaf from a plant lacking the mutation. In some embodiments, the at least one alkaloid is anatabine. In some embodiments, the method further includes selecting for progeny tobacco plants that comprise leaf that, when cured, exhibit a reduced amount of at least one TSNA relative to cured leaf from a plant lacking the mutation. In some embodiments, the at least one TSNA is NAT.

In still another aspect, a tobacco product is provided that includes cured leaf from a tobacco plant having a mutation in an endogenous nucleic acid having the sequence shown in SEQ ID NO: 7. In some embodiments, the leaf exhibits reduced expression or activity of QS relative to leaf from a plant lacking the mutation. In some embodiments, the leaf exhibits a reduced amount of at least one alkaloid relative to leaf from a plant lacking the mutation. A representative alkaloid is anatabine. In some embodiments, the cured leaf exhibits a reduced amount of at least one TSNA relative to cured leaf from a plant lacking the mutation. A representative TSNA is NAT.

In one aspect, a method of producing a tobacco product is provided. Such a method typically includes providing cured leaf from a tobacco plant having a mutation in an endogenous nucleic acid having the sequence shown in SEQ ID NO: 7; and manufacturing a tobacco product using the cured leaves. In some embodiments, the cured leaf exhibits reduced expression or activity of QS relative to cured leaf from a plant lacking the mutation. In some embodiments, the cured leaf exhibits a reduced amount of at least one alkaloid relative to cured leaf from a plant lacking the mutation. A representative alkaloid is anatabine. In some embodiments, the cured leaf exhibits a reduced amount of at least one TSNA relative to cured leaf from a plant lacking the mutation. A representative TSNA is NAT.

Any of the mutations described herein can include, without limitation, a point mutation, an insertion, a deletion, and a substitution.

In another aspect, a method of screening plants is provided. Such a method typically includes providing plant material from a plant as described herein; and determining the level of expression or activity of QS in the plant material. In still another aspect, a method of screening plants is provided. Such a method typically includes providing plant material from a plant as described herein; and determining the amount of at least one alkaloid in the plant material. In some embodiments, the at least one alkaloid is anatabine. In yet another aspect, a method of screening plants is provided. Such a method typically includes providing plant material from a plant as described herein; curing the plant material; and determining the amount of at least one TSNA in the plant material. In some embodiments, the at least one TSNA is NAT. In any of the methods described herein, the plant tissue can be leaf.

In another aspect, a method of identifying a tobacco plant or tobacco germplasm having a low or ultra-low anatabine phenotype is provided. Such a method typically includes detecting, in a tobacco plant or tobacco germplasm, at least one simple sequence repeat (SSR) of a marker locus that is associated with the phenotype, wherein the marker locus is represented by at least one of SEQ ID NOs: 1-6 or displays a recombination frequency of less than 10% with respect to a marker locus represented by at least one of SEQ ID NOs: 1-6 and maps to Linkage Group 6. In some embodiments, the detecting includes amplifying the marker locus or a portion of the marker locus with a primer pair and detecting the resulting amplicon. Representative primer pairs include, without limitation, SEQ ID NOs: 9 and 10, 11 and 12, 13 and 14, 15 and 16, 17 and 18, and 19 and 20.

In another aspect, a method of breeding is provided that includes crossing the tobacco plant or germplasm identified by a method described herein with a second tobacco plant or germplasm. In some embodiments, such a method further includes one or more steps of backcrossing, selfing, outcrossing, and selection of progeny plants. In some embodiments, such a method further includes the step of performing molecular marker analysis on DNA samples isolated from one or more progeny plants, wherein said analysis identifies a plant that includes at least one SSR selected from the group consisting of SEQ ID NOs: 1-6, wherein the SSR is associated with reduced amounts of anatabine in the progeny plants. In some embodiments, such a method further includes determining the amount of anatabine in leaf of the identified plant.

In yet another aspect, a method for detecting the presence of a marker linked to a gene associated with low or ultra-low anatabine in a tobacco plant is provided. Such a method typically includes analyzing chromosome 6 of the tobacco plant and detecting the presence of at least one SSR marker having a sequence selected from the group consisting of SEQ ID NOs: 1-5 and 6, and linked to a gene associated with low or ultra-low anatabine, wherein the presence of the at least one marker is indicative of a plant that exhibits low or ultra-low amounts of anatabine.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 4 is an alignment of a portion of the QS sequence containing the mutations (SEQ ID NOs: 45-56 (top to bottom)).

FIG. 5 is an alignment of QS sequences (SEQ ID NOs: 34-44 (top to bottom)).

DETAILED DESCRIPTION

Figure 1:
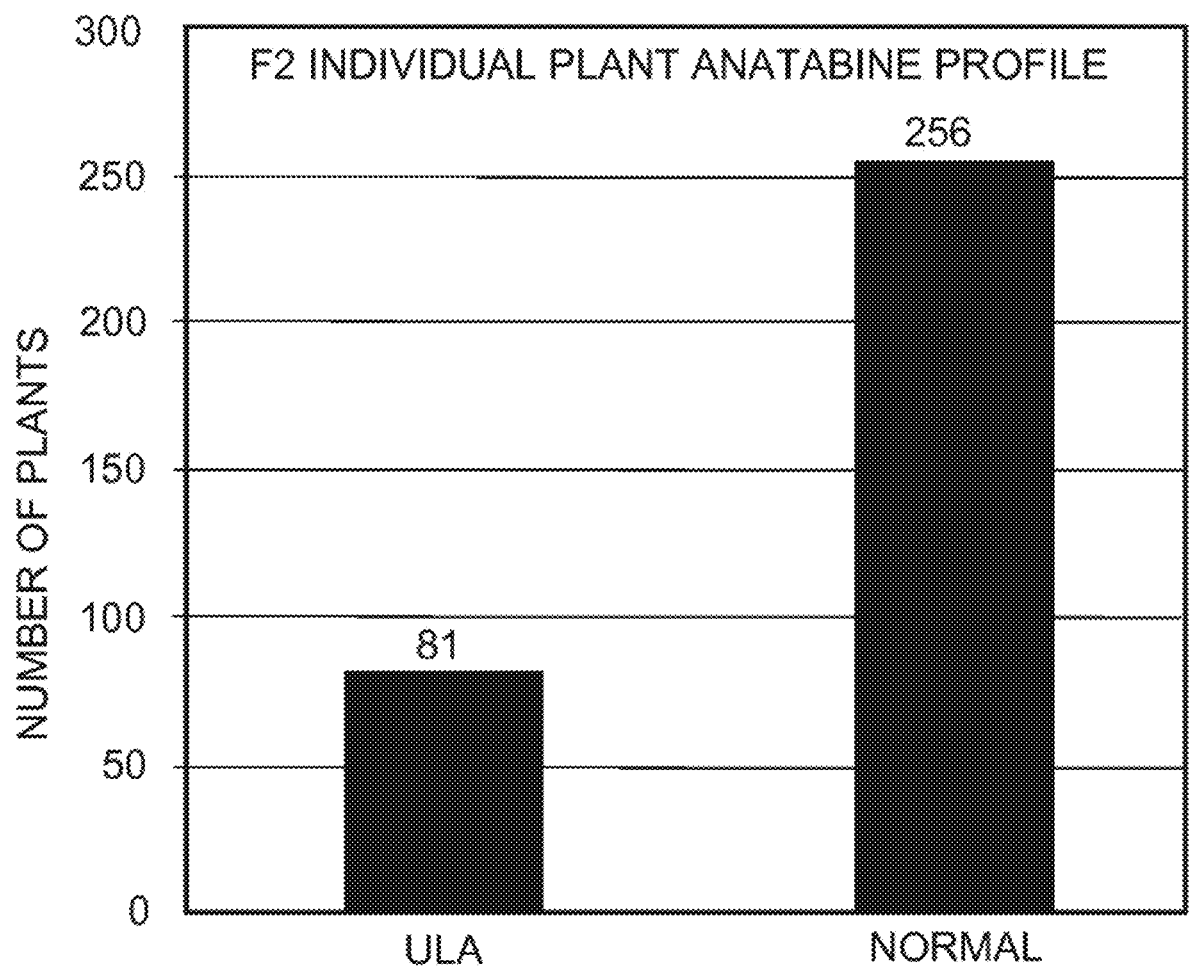
FIG. 1 is a graph showing the anatabine profiles of F2 individual plants.

Currently, there are no commercial tobacco varieties that exhibit reduced amounts of anatabine, and, prior to this disclosure, there were no known markers or genes associated with an ultra-low anatabine trait or even a low anatabine trait. As used herein, tobacco plants carrying an "ultra-low anatabine" trait (i.e., "ultra-low anatabine plants") are those plants having about 10% or less (e.g., about 9%, about 8%, about 7%, about 6%, about 5%, about 4%, about 3%, about 2%, about 1% or less (e.g., about 0%)) of the amount of anatabine that is typically present in a reference variety as shown in Table 1.

TABLE 1

Reference Varieties

| Types | Reference Varieties |
| --- | --- |
| Burley | TN 90 LC, KT 204 LC, TN 86 LC, KDH959 |
| Dark | KY171, NL Madole, VA359, TR Madole |
| Flue | K326, K346, K394 |
| Oriental | Izmir, Basma Drama, Basma Zihna I, |
| Maryland | Maryland 609, Maryland 60, Maryland TI228 |
| Cigar | Caujaro, Florida 2612, Galpao |

A skilled artisan would appreciate that this corresponds to a reduction in the amount of anatabine, relative to a reference variety tobacco plant, by at least about 90% (e.g., at least about 91%, about 92%, about 93%, about 94%, about 95%, about 96%, about 97%, about 98%, about 99% or about 100% reduction)). As used herein, tobacco plants carrying a "low anatabine" trait (i.e., "low anatabine plants") are those plants having between about 50% and about 89% (e.g., between about 55% and about 85%, between about 60% and about 80%, between about 65% and about 75%, between about 50% and about 75%, between about 50% and about 60%, between about 60% and about 70%, or between about 70% and about 89%) of the amount of anatabine that is typically present in a reference variety tobacco plant. A skilled artisan would appreciate that this corresponds to a reduction in the amount of anatabine, relative to a reference variety tobacco plant, of between about 11% and about 50% (e.g., between about 15% and about 45%, between about 20% and about 40%, between about 25% and about 35%, between about 15% and about 30%, between about 25% and about 45%, or between about 30% and about 50%).

As described herein, six simple sequence repeat (SSR) markers were identified that are tightly linked with the low anatabine trait in *Nicotiana tabacum*. The sequence of each of these markers is shown in SEQ ID NOs: 1-6. These markers can be used for breeding the low anatabine trait into varieties of interest. The genetic markers described herein also were used to identify the coding sequence associated with the locus. The gene was identified as quinolinate synthase (QS); the nucleic acid sequence of the cDNA is shown in SEQ ID NO: 7, while the encoded polypeptide is shown in SEQ ID NO: 8. Based on this discovery, the level of expression and/or the function of QS can be modulated in *N. tabacum*, thereby modulating the amount of TSNAs, particularly NAT, in cured tobacco and the resulting tobacco products.

Nucleic Acids and Polypeptides

A nucleic acid encoding wild type quinolinate synthase is provided herein (see, for example, SEQ ID NO: 7). As used herein, nucleic acids can include DNA and RNA, and includes nucleic acids that contain one or more nucleotide analogs or backbone modifications. A nucleic acid can be single stranded or double stranded, which usually depends upon its intended use. The wild type quinolinate synthase nucleic acid provided herein encodes a wild type quinolinate synthase polypeptide (see, for example, SEQ ID NO: 8).

Also provided are nucleic acids and polypeptides that differ from the wild type quinolinate synthase nucleic acid and polypeptide sequence (i.e., SEQ ID NO: 7 and 8, respectively). Nucleic acids and polypeptides that differ in sequence from SEQ ID NO: 7 and SEQ ID NO: 8 can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NO: 7 and 8, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 3, 5, 7, 9, 11, 13, 15, 17, 19, 21, 23, 25, 27, 29, 31, 33, 35, 37, 39, 41, 43, 45, 47, or 49), thereby leading to changes in the amino acid sequence of the encoded polypeptide (e.g., SEQ ID NOs: 2, 4, 6, 8, 10, 12, 14, 16, 18, 20, 22, 24, 26, 28, 30, 32, 34, 36, 38, 40, 42, 44, 46, 48, or 50). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain, and a "non-conservative amino acid substitution" is one in which an amino acid residue is replaced with an amino acid residue that does not have a similar side chain. See, for example, Dayhoff et al. (1978, in Atlas of Protein Sequence and Structure, 5(Suppl. 3):345-352), which provides frequency tables for amino acid substitutions.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame). Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Vectors as described herein can be introduced into a host cell. As used herein, "host cell" refers to the particular cell into which the nucleic acid is introduced and also includes the progeny or potential progeny of such a cell. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, CA).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Plants Having Reduced Amounts of NAT in Leaf and Methods of Making

Tobacco hybrids, varieties, lines, or cultivars are provided that have a mutation in an endogenous quinolinate synthase nucleic acid (e.g., SEQ ID NO: 7). The quinolinate synthase A protein (NadA) is a component of the quinolinate synthase complex, which includes quinolinate synthase A protein and L-aspartate oxidase protein. L-aspartate oxidase (NadB) is an FAD-dependent enzyme catalyzing the oxidation of L-aspartate to iminoaspartate Iminoaspartate is then condensed with DHAP to form quinolinate under the action of quinolinate synthase A, the gene product of nadA.

As described herein, leaf from plants having a mutation in one or more of the endogenous nucleic acids (e.g., SEQ ID NO: 7) can exhibit a reduced amount of alkaloids (e.g., anatabine) and/or TSNAs (e.g., NAT) compared to leaf from a plant that lacks the mutation. In addition, leaf from plants having a mutation in an endogenous quinolinate synthase nucleic acid (e.g., SEQ ID NO: 7) can exhibit a reduced amount of alkaloids or TSNAs (e.g., compared to leaf from a plant lacking the mutation).

Methods of detecting one or more alkaloids and one or more TSNAs, and methods of determining the amount of one or more alkaloids and one or more TSNAs, are known in the art. For example, high performance liquid chromatography (HPLC)-mass spectroscopy (MS) (HPLC-MS) or high performance thin layer chromatography (HPTLC) can be used to detect the presence of and/or determine the amount of alkaloids or TSNAs. In addition, any number of chromatography methods (e.g., gas chromatography/thermal energy analysis (GC/TEA), liquid chromatography/mass spectrometry (LC/MS), and ion chromatography (IC)) can be used to detect the presence of and/or determine the amount of alkaloids or TSNAs.

Methods of making a tobacco plant having a mutation are known in the art. Mutations can be random mutations or targeted mutations. For random mutagenesis, cells (e.g., *Nicotiana tabacum* cells) typically are mutagenized using, for example, a chemical mutagen or ionizing radiation. Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.*, 39(14):6315-25) or zinc-finger (see, for example, Wright et al., 2005, *The Plant J.*, 44:693-705). Whether random or targeted, a mutation can be a point mutation, an insertion, a deletion, a substitution, or combinations thereof.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those conserved regions would likely have little to no effect on polypeptide function. In addition, a mutation in a single nucleotide can create a stop codon, which would result in a truncated polypeptide and, depending on the extent of truncation, loss-of-function.

Preferably, a mutation in one of the novel nucleic acids disclosed herein results in reduced or even complete elimination of quinolinate synthase activity in a tobacco plant comprising the mutation. Suitable types of mutations in a quinolinate synthase coding sequence include, without limitation, insertions of nucleotides, deletions of nucleotides, or transitions or transversions in the wild-type quinolinate synthase coding sequence. Mutations in the coding sequence can result in insertions of one or more amino acids, deletions of one or more amino acids, and/or non-conservative amino acid substitutions in the encoded polypeptide. In some cases, the coding sequence comprises more than one mutation or more than one type of mutation.

Insertion or deletion of amino acids in a coding sequence, for example, can disrupt the conformation of the encoded polypeptide. Amino acid insertions or deletions also can disrupt sites important for recognition of the binding ligand (e.g., DHAP). It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the transporter polypeptide, introduce a stop codon to produce a truncated polypeptide, or disrupt an active site or domain (e.g., a catalytic site or domain, a binding site or domain) within the polypeptide.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Following mutagenesis, $M_0$ plants are regenerated from the mutagenized cells and those plants, or a subsequent generation of that population (e.g., $M_1$, $M_2$, $M_3$, etc.), can be screened for a mutation in a quinolinate synthase nucleic acid sequence (e.g., SEQ ID NO: 7). Screening for plants carrying a mutation in a sequence of interest can be performed using methods routine in the art (e.g., hybridization, amplification, combinations thereof) or by evaluating the phenotype (e.g., detecting and/or determining the amount of anatabine and/or NAT in the roots and/or the leaf). Generally, the presence of a mutation in a quinolinate synthase nucleic acid (e.g., SEQ ID NO: 7) results in a reduction of anatabine in the leaf of the mutant plants and NAT in the cured leaf of the mutant plants compared to a corresponding plant (e.g., having the same varietal background) lacking the mutation.

As used herein, "reduced" or "reduction" refers to a decrease (e.g., a statistically significant decrease) in the amount of anatabine in tobacco leaf, either green or cured, and/or NAT in cured leaf by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the mutation. As used herein, statistical significance refers to a p-value of less than 0.05, e.g., a p-value of less than 0.025 or a p-value of less than 0.01, using an appropriate measure of statistical significance, e.g., a one-tailed two sample t-test.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype. Such plants may be heterozygous and exhibit a mutant phenotype due to a phenomenon such as dominant negative suppression, despite the presence of the wild type allele, or such plants may be homozygous due to independently induced mutations in both alleles.

A tobacco plant carrying a mutant allele can be used in a plant breeding program to create novel and useful cultivars, lines, varieties and hybrids. Thus, in some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Breeding is carried out using known procedures. DNA fingerprinting, SNP or similar technologies may be used in a marker-assisted selection (MAS) breeding program to transfer or breed mutant alleles into other tobaccos, as described herein. Progeny of the cross can be screened for a mutation using methods described herein, and plants having a mutation in a quinolinate synthase nucleic acid sequence (e.g., SEQ ID NO: 7) can be selected. For example, plants in the $F_2$ or backcross generations can be screened using a marker developed from a sequence described herein or a fragment thereof, using one of the techniques listed herein. Leaf (green or cured, as appropriate) from progeny plants also can be screened for the amount of anatabine and/or NAT, and those plants having reduced amounts, compared to a corresponding plant that lacks the mutation, can be selected. Plants identified as possessing the mutant allele and/or the mutant phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, confirmation of the null condition, and/or chemical analyses of leaf (e.g., cured leaf) to determine the level of anatabine and/or NAT.

The result of a plant breeding program using the mutant tobacco plants described herein are novel and useful cultivars, varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development.

Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

As used herein, the term "cultivar" refers to a uniform variety, strain or race of plant selected for desirable characteristics that are maintained by vegetative propagation or by inbred seed.

The tobacco plants used in the methods described herein can be a Burley type, a dark type, a flue-cured type, a Maryland type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF157, GF318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

In addition to mutation, another way in which the amount of anatabine and NAT in tobacco leaf can be reduced is to use inhibitory RNAs (e.g., RNAi). Therefore, transgenic tobacco plants are provided that contain a transgene encoding at least one RNAi molecule, which, when transcribed, silences an endogenous quinolinate synthase nucleic acid (e.g., SEQ ID NO: 7). It would be understood in the art that "silencing" can refer to complete elimination or essentially complete elimination of the quinolinate synthase mRNA, resulting in 100% or essentially 100% reduction (e.g., greater than 95% reduction; e.g., greater than 96%, 97%, 98% or 99% reduction) in the amount of quinolinate synthase polypeptide; silencing also can refer to partial elimination of the quinolinate synthase mRNA (e.g., eliminating about 5%, 10%, 15%, 20%, 25%, 30%, 35%, 40%, 45%, 50% or more of the quinolinate synthase mRNA), resulting in a reduction (e.g., about 5%, 10%, 15%, 20%, 25%, 30%, 35%, 40%, 45%, 50% or more, but not complete elimination) in the amount of the quinolinate synthase polypeptide. As described herein, leaf from such transgenic plants exhibit a reduced amount of anatabine and NAT (e.g., compared to leaf from a plant lacking or not transcribing the RNAi).

RNAi technology is known in the art and is a very effective form of post-transcriptional gene silencing. RNAi molecules typically contain a nucleotide sequence (e.g., from about 18 to about 50 nucleotides in length) that is complementary to the target gene in both the sense and antisense orientations. The sense and antisense strands can be connected by a short "loop" sequence (e.g., about 5 to about 20 nucleotides in length) and transcribed in a single transcript, or the sense and antisense strands can be delivered to and transcribed in the target cells on separate vectors or constructs. A number of companies offer RNAi design and synthesis services (e.g., Life Technologies, Applied Biosystems).

The RNAi molecule can be transcribed using a plant expression vector. The RNAi molecule typically is at least 25 nucleotides in length and has at least 91% sequence identity (e.g., at least 95%, 96%, 97%, 98% or 99% sequence identity) to a quinolinate synthase nucleic acid sequence disclosed herein (e.g., SEQ ID NO: 7) or hybridizes under stringent conditions to a quinolinate synthase nucleic acid sequence disclosed herein (e.g., SEQ ID NO: 7). Hybridization under stringent conditions is described above.

Methods of introducing a nucleic acid (e.g., a heterologous nucleic acid) into plant cells are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation. Following transformation, the transgenic plant cells can be regenerated into transgenic tobacco plants. As described herein, transcription of the transgene results in leaf that exhibits a reduced amount of anatabine or NAT in the resulting cured leaf relative to leaf from a plant not transcribing the transgene. The leaves of the regenerated transgenic plants can be screened for the amount of anatabine or NAT in the resulting cured leaf, and plants having reduced amounts of anatabine or NAT in the resulting cured leaf, compared to the amount in a corresponding non-transgenic plant, can be selected for use in, for example, a breeding program as discussed herein.

Nucleic acids that confer traits such as herbicide resistance (sometimes referred to as herbicide tolerance), insect resistance, or stress tolerance, can also be present in the novel tobacco plants described herein. Genes conferring resistance to a herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 20010016956.

A number of genes are available that confer resistance to insects, for example, insects in the order Lepidoptera. Exemplary genes include those that encode truncated Cry1A(b) and Cry1A(c) toxins. See, e.g., genes described in U.S. Pat. Nos. 5,545,565; 6,166,302; and 5,164,180. See also, Vaeck et al., 1997, Nature, 328:33-37 and Fischhoff et al., 1987, Nature Biotechnology, 5:807-813. Particularly useful are genes encoding toxins that exhibit insecticidal activity against *Manduca sexta* (tobacco hornworm); *Heliothis virescens* Fabricius (tobacco budworm) and/or *S. litura* Fabricius (tobacco cutworm).

Plants Having Increased Amounts of Anatabine in Leaf and Methods of Making

The sequences described herein can be overexpressed in plants in order to increase the amount of anatabine in the leaf. Therefore, transgenic tobacco plants, or leaf from such plants, are provided that include a plant expression vector. A plant expression vector typically includes a quinolinate synthase nucleic acid molecule described herein (e.g., SEQ ID NO: 7) or a functional fragment thereof under control of a promoter that is able to drive expression in plants (e.g., a plant promoter). As discussed herein, a nucleic acid molecule used in a plant expression vector can have a different sequence than a sequence described herein, which can be expressed as a percent sequence identity (e.g., relative to SEQ ID NO: 7) or based on the conditions under which the sequence hybridizes to SEQ ID NO: 7.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein, one of skill in the art can predict the portion(s) of a polypeptide (e.g., one or more domains) that may impart the desired functionality.

Following transformation, the transgenic tobacco cells can be regenerated into transgenic tobacco plants. The leaves of the regenerated tobacco plants can be screened for the amount of anatabine, and plants having increased amounts of anatabine, compared to the amount in a corresponding non-transgenic plant, can be selected and used, for example, in a breeding program as discussed herein. Expression of the nucleic acid molecule or a functional fragment thereof may result in leaf that exhibits an increased amount of anatabine compared to leaf from a tobacco plant that does not express the nucleic acid molecule or functional fragment thereof.

Genetic Markers of Low-/Ultra-Low-Anatabine Trait in Tobacco

Although coding sequences (i.e., the sequences that encode a protein) generally are well-conserved within a species, non-coding regions tend to accumulate polymorphism, and, therefore, can vary between individuals of the same species. Such regions provide the basis for genetic markers. In general, any differentially-inherited nucleic acid polymorphism that segregates among progeny is a potential genetic marker. The genomic variability that results in a genetic marker can be of any origin, including insertions, deletions, duplications, repetitive elements, point mutations, recombination events, and the presence and sequence of transposable elements.

In general, the identification of markers for MAS application involves determining the phenotype of the trait(s) of interest and genotyping the segregating population of progenies using polymorphic markers and genetic mapping of the desired trait. Details of mapping are described elsewhere herein. Polymorphic loci in the vicinity of the mapped trait are chosen as potential markers (typically, a marker locus closest to the locus of interest is a preferred marker). Linkage analysis is then used to determine which polymorphic marker allele sequence demonstrates a statistical likelihood of co-segregation with the desirable phenotype (thus, a "marker allele"). It is then possible to use this marker for rapid, accurate screening of plant lines for the marker allele without the need to grow the plants through their life cycle and await phenotypic evaluations.

Numerous methods for detecting genetic markers also are well-established. Markers corresponding to genetic polymorphisms between members of a population can be detected by numerous methods that are well-established in the art such as, without limitation, restriction fragment length polymorphisms, isozyme markers, allele specific hybridization (ASH), amplified variable sequences of the plant genome, self-sustained sequence replication, simple sequence repeats (SSRs), single nucleotide polymorphisms (SNPs), or amplified fragment length polymorphisms (AFLPs). The genetic markers described herein are SSRs. See, for example, any of SEQ ID NOs:1-6.

Genetic markers can facilitate mapping and selection of agriculturally important traits. A genetic marker that demonstrates linkage disequilibrium with a desired trait (e.g., low- or ultra-low-anatabine) can be a useful tool for marker-assisted selection (MAS), providing a means for rapid identification of desirable individuals or lines. Introgression of one or more particular genes into a cultivar or variety also can be facilitated by MAS. Simply by way of example, MAS can include the steps of (i) creating a map of genetic markers; (ii) determining statistical associations between one or more genetic markers and a phenotype (or phenotypic variability); (iii) identifying/defining a set of genetic markers associated with the phenotype (or phenotypic variability); and (iv) applying this information to a breeding program.

MAS can be used in plant breeding to assist in the efficient recovery of, for example, the recurrent parent genotype following backcrossing. In marker-assisted backcrossing, progeny can be selected for the donor trait (e.g., low- or ultra-low anatabine) and then repeatedly backcrossed to, for example, an elite line to reconstitute as much as possible of the elite line's background.

Tobacco Products and Methods of Making

The methods described herein allow for leaf constituents in a tobacco plant to be altered. As described herein, altering leaf constituents refers to reducing the amount of one or more alkaloids (e.g., anatabine) or one or more TSNAs (e.g., NAT) in the leaf or increasing the amount of one or more alkaloids (e.g., anatabine) in the leaf. As described herein, such methods can include mutagenesis (e.g., random or targeted) or the production of transgenic plants (using, e.g., RNAi or overexpression).

Leaf from such tobacco (e.g., having reduced amounts of one or more alkaloids or one or more TSNAs or increased amounts of one or more alkaloids) can be cured, aged, conditioned, and/or fermented. Methods of curing tobacco are well known and include, for example, air curing, fire curing, flue curing and sun curing. Aging also is known and typically is carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993, 4,660,577, 4,848,373 and 5,372,149. The tobacco also can be further processed (e.g., cut, expanded, blended, milled or comminuted), if desired, and used in a tobacco product.

Tobacco products are known in the art and include any product made or derived from tobacco that is intended for human consumption, including any component, part, or accessory of a tobacco product. Representative tobacco products include, without limitation, smokeless tobacco products, tobacco-derived nicotine products (e.g., tobacco-derived nicotine pieces for use in the mouth), cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, cut tobacco, electronic cigarettes, electronic cigars, electronic cigarillos, and e-vapor devices. Representative smokeless tobacco products include, for example, chewing tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the reduced-alkaloid tobacco, the reduced-TSNA tobacco, or the increased-alkaloid tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Mutagenesis

Since the biosynthetic pathway of anatabine and its associated genes is not completely known, a novel genetic variation was created in a population of tobacco plants to identify plants that have a significantly reduced ability to biosynthesize anatabine. These plants very likely have a mutated non-functional gene, critical for anatabine biosynthesis.

A population of the Flue-cured variety "401" was used in these experiments. Approximately 5000 seeds were treated with 0.6% ethyl methane sulfonate and germinated. M1 plants were grown in the field and M2 seeds were collected. Fifteen hundred M2 seeds were germinated and grown in 4-inch pots. At 50% flowering stage, plants were topped. Leaf samples were collected 2 weeks after topping and the samples screened for anatabine levels using high performance thin layer chromatography (HP-TLC) and gas chromatography.

After screening for alkaloids, two Flue Cured (FC) 401 ultra-low anatabine (ULA) lines were selected for trait development. It is noted that the amount of nicotine in both ULA lines is unchanged.

Example 2—Identification of Genetic Markers

To identify genetic marker(s) associated with the ULA trait, test crosses of FC401 mutant #1 (MS4144) were made with variety Red Russian and the F1s were selfed to generate F2 seed. Three hundred and thirty seven F2 plants were grown in the field and the alkaloids were analyzed individually. Depending on the anatabine levels, the mapping populations were grouped into ULA plants and normal plants (FIG. 1). Genomic DNA from each of the plants was extracted individually. To run simple sequence repeat (SSR) markers, DNA samples from 23 F2 ULA plants and 24 normal anatabine plants were pooled separately.

PCR reactions were performed in 25 µl final volumes which contained 25-50 ng of template DNA, 12.5 µl 2× Amplitag PCR master mix ((Applied Biosystems [ABI]), 0.2 µM labeled primers (ABI), 1 µl 100% DMSO (Fisher Scientific), and 8 µl $H_2O$ (DNase/RNase free). Thermocycling conditions consisted of a 15 min incubation at 95° C.; followed by 34 cycles of 1 min at 94° C., 2 min at 60° C., 1 min at 72° C.; with a final reaction step of 60° C. for 30 min. All completed PCR reactions were diluted 1:50 with deionized water. Two microliters of diluted product was then combined with 9.75 µl HiDi Formamide (ABI) and 0.25 µl GeneScan 500 LIZ (ABI) size standard. Fragment analyses were performed. Samples were separated using a 36 cm capillary array in an ABI 3730 DNA Analyzer. Generated amplicons were analyzed using the "Local Southern Method" and the default analysis settings within GeneMapper v. 3.5 software (ABI). Final allele calls were standardized to an internal DNA control and based on the ABI 3730 DNA Analyzer.

Example 3—Linkage Mapping

A representative set of 246 SSR markers were selected and assessed in mapping parental lines (FC401× Red Russian). Of the 246 markers, 239 showed polymorphism among parents and were mapped and assessed for ULA trait screening. Six of those markers showed polymorphisms among ULA and non ULA traits and were tightly linked to the ULA trait. The six genetic markers are shown in Table 2, and all were found to be located on chromosome 6. Sequence information of the primer sets that were used are listed in Table 3.

TABLE 2

SSR markers tightly linked with ULA trait

| SSR Designation | SSR Sequence | SEQ ID NO |
|---|---|---|
| PT61163 | AGTGGCGGAGGTAGGAATTTCACCAAGAGAATTCAAA AAAATAAAAGTATACATGCAAAGAAGCAAACGTGATT CATCACCTAATATATATATATATATATATATATATAT ATATATATATATATATATATATATATATATATATACA TATACATAAAAATAAAATTTGACTTTATATACATAGT GTAATTTCCCGGCTACCTCACTCTTA | 1 |
| PT60043 | CCCTTTGCCACTTTACAAGAATTTTCCCTCATGTCGAG GGGATTCAACAGCTTTTATATATATATATATATATA AAGGAAAAAAGTAGTTGTTATCCTATTTGCACAA | 2 |
| PT60878 | AGCTCCATTTGTACTTCCGCGAGCGAGGTTCCAGACAG CCTATTTAATAATATATATATATATATATATATATATT CACAAATATTGTGTATATACTACATACACACACATATA TAAAGTGTGCATAGTGTAAACAATAGCTCACTTATTCA CATAAGACTTAAGTTTGTATAATCATCTTGGAACGTCT GTTAGAA | 3 |
| PT61060 | CACAAGACCCTTCTTGGTGCTGTAGAAATTGAAAGAAAT GCAAAGGCTTTTTTTCTACTCTATCCTGTATTTCAATGT TTGGTGTGATTAAGCTATTATGCAGAATTTTGTATAGCA AGGAACCATATATATATATATATATATATATATATATAT ATATACTAGACAGGGTTGCTGCCCAAAATATTAGGCGTG AAGCCTGTCTTGGTGGCAATATCAATAGTGCTCCGCCCA AAATATTAGGCGTGAAGCCTGTCTT | 4 |
| PT60925 | CAGAGATTACACCCATTGTGCTTCTTTTTAAAGGAGTAAA GTGGGAAAAAATCACCAAATACTTGAATAAAGACAGAGAA TAACCCCTCTCTCTCTCTCTCTCACACACACTCCTTTT TCGGCATTTATATTATAGAGCACACAGACAATAGATCTAT GGGTGAGAAAGATACTATTACTACCTACATTGACGGCGG | 5 |
| PT50801 | TGTCTCAACTTCTTGTCAATTGCTAATCACTCTTTTTATG GAATTGACATGCTACATATATATATATATATATATATA TTACTTTTCTTAGCAAATATATTTATAAGTATCGCAGGAT GACATAATAAGG | 6 |

TABLE 3

Primers used to detect the SSR markers

| Primer | Forward Primer | SEQ ID NO | Reverse Primer | SEQ ID NO |
|---|---|---|---|---|
| PT61163 | AGTGGCGGAGGTAGGAATTT | 9 | TAAGAGTGAGGTAGCCGGGA | 10 |
| P160043 | CCCTTTGCCACTTTACAAGAA | 11 | TTGTGCAAATAGGATAACAACTACTTT | 12 |
| P160878 | AGCTCCATTTGTACTTCCGC | 13 | TTCTAACAGACGTTCCAAGATGA | 14 |
| P161060 | CACAAGACCCTTCTTGGTGC | 15 | ACGTGGAGTGGAGAAACCAG | 16 |
| P160925 | CAGAGATTACACCCATTGTGCT | 17 | CCGCCGTCAATGTAGGTAGT | 18 |
| P150801 | TGTCTCAACTTCTTGTCAATTGCT | 19 | CCTTATTATGTCATCCTGCGA | 20 |

Figure 2:
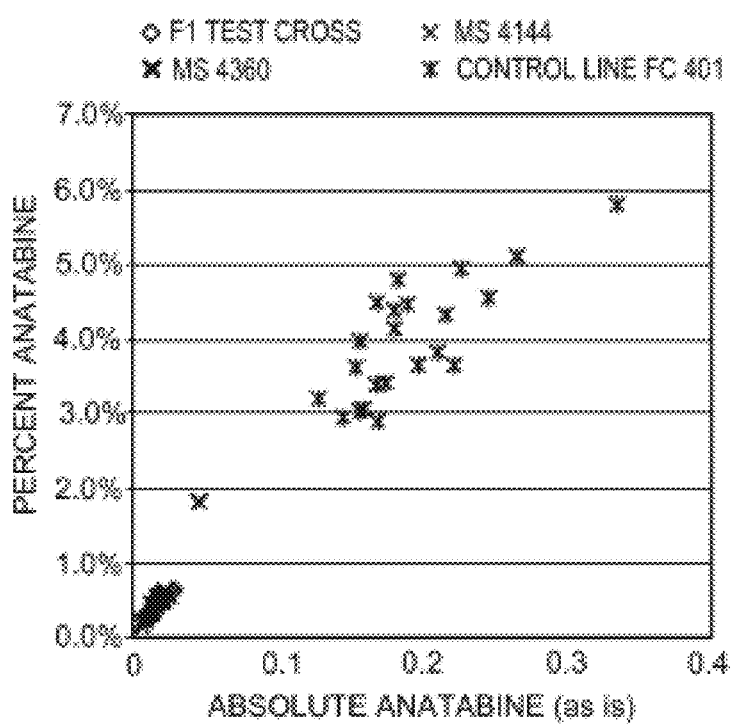
FIG. 2 depicts the results of experiments performed to examine the inheritance pattern of anatabine. Panel A shows the anatabine inheritance profile and Panel B is a graph showing the average percentage of anatabine for an F1 cross between the FC401 mutant #1 (MS4144)×FC401 Mutant #2 (MS4360).
Figure 2:
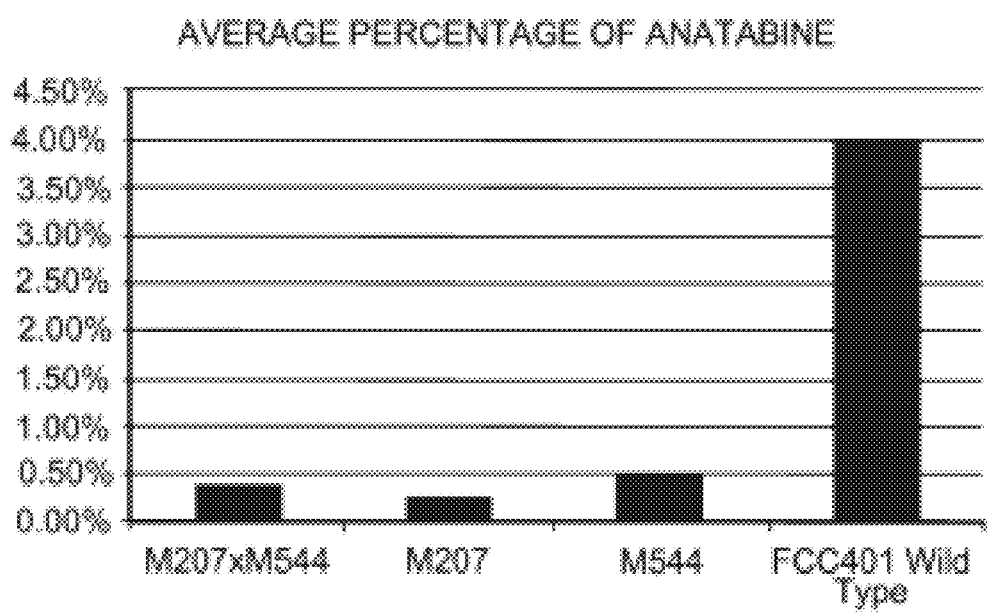

To evaluate the nature of the mutant gene in the FC401 ULA mutant #2, a cross between the FC401 mutant #1 and FC401 mutant #2 was made and the alkaloids were analyzed in the F1 generation. Even though they are two independent lines, the anatabine profile of F1 plants showed that they are mutants for the same gene (FIGS. 2A and 2B). Therefore, anatabine profile and genetic marker analysis indicate that a single recessive gene is critical for anatabine biosynthesis and is located on genetic linkage map 6.

Example 4—Identifying Candidate Genes

A list of candidate target genes that may be responsible for the low anatabine trait were generated from the following three different sets of gene expression data, as follows.
A) Methyl jasmonate up-regulated genes: Six samples of *Nicotiana tabacum* cultivar Bright Yellow—2, in two treatment groups of 3 samples each, are examined for gene expression. The first group consists of mock-treated control samples (CTR) obtained at 0, 48 and 72 hrs post-treatment. The second group consists of samples treated with methyl jasmonate and obtained at the same time points. Samples are analyzed by microarray (Cogenics), and log-ratio p-values and fold-changes for each probe are determined by Rosetta Resolver using the Agilent/Intensity—Pairwise Ratio Builder. These values are used to compare with the datasets from B) and C).
B) Topping up-regulated root expression genes: Forty eighty tobacco plants of the VA359 tobacco variety are grown in 10-inch pots. At 50% flowering, plants are topped; root samples are collected just before topping and at 30 mins, 2 hrs, 6 hrs, 12 hrs, 24 hrs, 72 hrs and 1 week post-topping. Six plants per time point are used for sample collection. Total RNA is isolated individually, equal amounts are pooled for each time point, and the samples hybridized with the tobacco microarray (Nimblegen). Log-ratio p-values and fold-changes for each array are determined by Rosetta Resolver using the Agilent/Intensity—Pairwise Ratio Builder. These values are used to compare with datasets from A) and C).
C) Methyl jasmonate up-regulated proteins: Triplicate samples of BY2 cells are mock-treated or treated with methyl jasmonate for 12, 24, and 48 hrs. Proteins from these samples are extracted and proteomic analysis is done by Biognosys Inc. Briefly, total proteins from the samples are used to produce a master list of all possible proteins that can be detected by the assay. Individual samples are then subjected to quantitative mass spectroscopy, and differential protein expression levels among each sample are generated. These values are used to compare gene expression profiles among the datasets from A) and B).

Example 5—Screening and Cloning Candidate Genes

Figure 3:
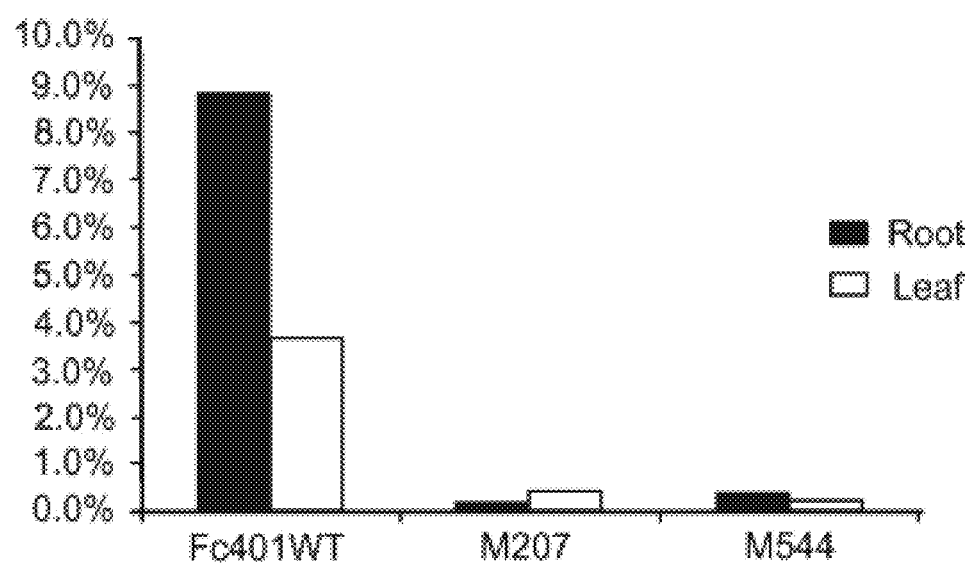
FIG. 3 is a graph showing the amount of anatabine in the root and leaf of reference variety tobacco plants and the two mutant tobacco plants.

Three tobacco lines, FC401 wild type (Wt); FC40-M207 mutant line fourth generation (M4) and FC401-M544 mutant line fourth generation (M4) were used for candidate gene screening. Low anatabine traits were confirmed for the two tobacco mutant lines (M207 and M544) in root and leaf before screening (see FIG. 3).

RNA was extracted from root tissues of wild type (Wt) FC401, M207 and M544 with RNeasy Plus Mini kit from Quiagen Inc. following the manufacturer's protocol. cDNA libraries were prepared from the RNAs using In-Fusion® SMARTer® Directional cDNA Library Construction Kit from Clontech Inc. cDNA libraries were diluted to 100 ng/μl and used as the template for candidate gene PCR screening.

PCR amplifications were performed in 50 μl final volumes that contained 50-100 ng of template DNA (i.e., the cDNA library) and 0.2 μM of primers (Fisher Scientific) using the Platinum® Taq DNA Polymerase High Fidelity kit (Life Technology Inc.). Thermocycling conditions included a 5 min incubation at 94° C.; followed by 34 cycles of 30 seconds at 94° C., 30 seconds at 58° C., 1 min 30 seconds at 68° C.; with a final reaction step of 68° C. for 7 mins. The PCR products were evaluated by agarose gel electrophoresis, and desired bands were gel purified and sequenced using an ABI 3730 DNA Analyzer (ABI).

51 candidate genes (listed in Table 4) were cloned from $F_{401}$, Wt, M207 and M544 lines, and sequenced for single nucleotide polymorphism (SNP) detection.

TABLE 4

Listing of Candidate Genes for Screening

| | |
|---|---|
| Quinolinate Synthase A-1 | Pathogenesis related protein 1 |
| Allene oxide synthase | Allene oxide cyclase |
| ET861088.1 Methyl esterase | FH733463.1 TGACG-sequence specific transcription factor |
| FH129193.1 Aquaporin-Transport | FH297656.1 Universal stress protein |
| Universal stress protein Tabacum sequence | FH077657.1 Scarecrow-like protein |
| FH864888.1 EIN3-binding F-box protein | FH029529.1 4,5 DOPA dioxygenase |
| FI010668.1 Ethylene-responsive transcription factor | EB430189 Carboxylesterase |
| DW001704 Glutathione S transferase | EB683763 Bifunctional inhibitor/lipid transfer protein/seed storage 2S albumin |
| DW002318 Serine/threonine protein kinase | DW004086 Superoxide dismutase |
| DW001733 Lipid transfer protein DIR1 | DW001944 Protein phosphatase 2C |
| DW002033 | EB683763 Bifunctional inhibitor/lipid transfer protein/seed storage 2S albumin |
| DW002318 Serine/threonine protein kinase | DW002576 Glycosyl hydrolase of unknown function DUF1680 |
| EB683279 | EB683763 |
| EB683951 | FG141784 (FAD Oxidoreductase) |
| BBLa-Tabacum sequences | BBLb |
| BBLc | BBLd |
| Pdr1 | Pdr2 |
| Pdr3 | Pdr5a |
| Pdr5b | NtMATE1 |
| NtMATE2 | NtMATE3 |
| WRKY8 | EIG-I24 |
| WRKY3 | WRKY9 |
| EIG-E17 | AJ748263.1 QPT2 quinolinate phosphoribosyltransferase |
| AJ748262.1 QPT1 | |

Example 6—SNP Detection and Characterization of the Mutants

Full length QS genes from the FC401 control and from the M207 and M544 mutant plants were cloned using AP23 and QSR1 primers which were designed using *N. benthamiana* QS gene sequence. The primer sequences are shown in Table 5. The cloned QS genes were sequenced and analyzed for mutations.

One SNP from M207 line and one SNP from M544 line were identified, and both SNPs were found to be located in the quinolinate synthase (QS) gene (FIG. 4).

In mutant line M544, the mutation is located 1546 nucleotides from the start codon. This G to A mutation results in an amino acid change from valine to isoleucine. In mutant line M207, the mutation is located 1460 nucleotides from the start codon. This G to A mutation results in an amino acid change from cysteine to tyrosine.

TABLE 5

Quinolinate Synthase Gene Screening Primers

| Name | Primer Sequence | SEQ ID NO |
| --- | --- | --- |
| AP23 | ATCTTTGCTTCCTCGACTCCA | 21 |
| AP24 | AGTTAAGCGGAGCTTGATCGT | 22 |
| AP23Seq1 | ATGAGGTGCTGGCGTTGA | 23 |
| AP23Seq2 | TTCAGCGTAGCTGCCTTG | 24 |
| AP23Seq3 | GGAGTTTATCGGATGTCG | 25 |
| AP23Seq4 | TGTGCAGTAAGGAATGCATC | 26 |
| AP23Seq5 | GTTGTGAGCCGGTTCTGCAC | 27 |
| AP235pEND | ATGGACGCCGCAAATTTAGTCATGA | 28 |
| AP29F1 | AGTGACTCGGAAATAACTAAAGGGTTTT | 29 |
| AP29R1 | AGTATTAGTCACAACATGCAGAGATGAG | 30 |
| AP29F2 | GAGCTCTTTCCATCTCTAGTAATCACA | 31 |
| AP29R2 | ATGTAGGTATCAGGACCATACAACACT | 32 |
| QSR1 | GTTCGAGGTAGAACCTACTAG | 33 |

```
Quinolinate Synthase ACDS - Fc401
                                                   (SEQ ID NO: 7)
ATGGATGCCGCAAATTTAGTCATGAAATCTTCCTTGTTTTCGAAATCCCCATGTCCCCTTTT

TAGTTCTAAACTCATTCCTAGAGCACCACCCTCTGTCTTTACTCTGCCTTCTACCTTTAGAC

CCCTCGTTAAATGCATACAAGCTTCATTCCCACCAAACCCTGATTCCAAAAAACCCTCAAAC

AATTCAACCTTTACGTGTTCAGCTGTGACTTCCTTCCCTTCTCAACAATCTCAGCCTCACGC

GCCTTCCGATGCCAAGCTCCAACTCCTGATCTCTGAATTCCAGTCCCTCGTCGAACCAATGG

ACCGCGTGAAACGCCTCTTGCACTACTCCACACTCCTCCCTCCAATGGACGCGTCCTTCAAA

ACCCCTGAGAATCGCGTACCGGGTTGCACTACACAGGTATGGCTGAACGTGAGTTTCGATGA

GGCTGAGAACAGGATGAAATTTTTGGCGGACAGTGACTCGGAAATAACTAAAGGGTTTTGCG

CGTGTTTGGTTTCGCTGCTGGACGGGGCTACTCCCGATGAGGTGCTGGCGTTGAAAACGGAG

GACTTGAATGCTTTGAATGTTGCGGGGTTGAACGGGAAAGGATCGGCATCTAGGGCGAATAC

GTGGCATAATGTGTTGGTCAGCATGCAGAAAAGGACAAGGGCCTTAGTTGCGGAGCGTGAAG

GCAGGCCGCGCGGCGAGCTCTTTCCATCTCTAGTAATCACAGCTGATGGTATCCAACCCCAA

GGCAGCTACGCTGAAGCCCAGGCAAGGTTCCTGTTTCCTGATGAATCAAGGGTCCAAAAACT

TGCCAATTTGCTAAAGGAGAAGAAAATAGGAGTTGTTGCTCATTTCTACATGGACCCTGAGG

TGCAAGGTGTTCTAACTGCAGCGCAGAAGCTTTGGCCCCATATACATATATCTGATTCTTTA

GTCATGGCTGATAAAGCTGTCAGTATGGCAAAAGCTGGATGTGAATATATATCTGTATTGGG

TGTAGATTTCATGTCAGAGAATGTGCGAGCCATTCTTGATCTAGCTGGATTCCCAGAGGTTG

GAGTTTATCGGATGTCGGACGAACGCATTGGTTGTTCTTTGGCTGATGCTGCAGCCAGCCCA

GCATACTTGGATTATCTTAAAACAGCTTCAACTTCTTCTCCATCTCTGCATGTTGTGTACAT

AAATACTTCACTGGAGACAAAAGCATATTCTCATGAGCTTGTTCCGACTATAACATGTACTT

CCTCTAATGTTGTGCAAACTATTCTGCAGGCATTTGCTGAAGTACCTGACTTGGAAGTGTTG

TATGGTCCTGATACCTACATGGGTTCAAACATTGCGGAATTGTTCACCCAGATGTCCACGAT

GACTGATGAAGAAATTTCTGCGATACATCCTTTGCACAACAGAATCTCCATTAAATCTTTGC

TTCCTCGACTGCATTATTTTCAGGATGGGACATGTATTGTTCATCACCTCTTTGGTCATGAA

GTTGTGGAGAAGATAAATGAAATGTATGGGGATGCATTCCTTACTGCACACTTTGAAGTTCC

TGGTGAAATGTTTTCCCTGGCAATGGAAGCGAAGAAAAGGGGCATGGGAGTAGTAGGTTCTA

CCTCGAACATACTCGACTTTATCAAAGAAAGGGTAGAAGAGTCCTTGAATAGAAACGTAGAT
```

-continued

```
GAACATCTTCAGTTTGTTTTGGGAACGGAATCAGGAATGATTACGGCAATAGTTGCAGCAGT

CGGTAAATTACTAGGTTCTGCTGACTCCTCTTCCGGTGGAGCAAAAGTAAGTGTTGAGATTG

TCTTTCCTGTCTCGTCAGAATCAGTGACAAGAACATCTACGGGTTCGCCTCTGGACCAAAAT

AAGGTCAATATTATACCTGGAGTTGCAAGTGGAGAGGGGTGTTCTCTACATGGTGGATGTGC

CTCCTGTCCATATATGAAGATGAACTCTCTTAGCTCGTTGCTAAAAGTTTGCCAGAGCTTGC

CCCATGGCAAAGCCGAACTTTCAGCTTATGAGGCAGGACGATTCAGTTTGCGAACCCCCAAG

GGAAAACAAATTGCGGATGTTGGTTGTGAGCCGGTTCTGCACATGAGACACTTTCAGGCAAC

AAAGAGATTACCAGAGCAGCTAATCAATCAAATACTTCAACGATCAAGCTCTGCTTAA
```

(SEQ ID NO: 8)
```
MDAANLVMKSSLFSKSPCPLFSSKLIPRAPPSVFTLPSTFRPLVKCIQASFPPNPDSKKPSN

NSTFTCSAVTSFPSQQSQPHAPSDAKLQLLISEFQSLVEPMDRVKRLLHYSTLLPPMDASFK

TPENRVPGCTTQVWLNVSFDEAENRMKFLADSDSEITKGFCACLVSLLDGATPDEVLALKTE

DLNALNVAGLNGKGSASRANTWHNVLVSMQKRTRALVAEREGRPRGELFPSLVITADGIQPQ

GSYAEAQARFLFPDESRVQKLANLLKEKKIGVVAHFYMDPEVQGVLTAAQKLWPHIHISDSL

VMADKAVSMAKAGCEYISVLGVDFMSENVRAILDLAGFPEVGVYRMSDERIGCSLADAAASP

AYLDYLKTASTSSPSLHVVYINTSLETKAYSHELVPTITCTSSNVVQTILQAFAEVPDLEVL

YGPDTYMGSNIAELFTQMSTMTDEEISAIHPLHNRISIKSLLPRLHYFQDGTCIVHHLFGHE

VVEKINEMYGDAFLTAHFEVPGEMFSLAMEAKKRGMGVVGSTSNILDFIKERVEESLNRNVD

EHLQFVLGTESGMITAIVAAVGKLLGSADSSSGGAKVSVEIVFPVSSESVTRTSTGSPLDQN

KVNIIPGVASGEGCSLHGGCASCPYMKMNSLSSLLKVCQSLPHGKAELSAYEAGRFSLRTPK

GKQIADVGCEPVLHMRHFQATKRLPEQLINQILQRSSSA
```

There are 2787 QS genes listed in Pfam protein data base and 41 of the QS genes are from plants (The Pfam protein family database; Punta et al., Nuc. Acids Res., 2012, 40:D290-D301). The alignment that is shown in FIG. 5 compares the amino acid sequences of the wild type QS and the two mutant lines with respect to representative plant QS sequences. The M207 mutation (C to Y) is conserved in all but one of the 2787 QS sequences deposited in the Pfam database. The M544 mutation (V to I) is conserved only in plants and not in other QS genes.

To confirm the stability of the mutations, the QS gene was sequenced in multiple generations of mutants. The QS gene mutation patterns correlated with the anatabine levels of the mutant lines, indicating that the QS gene mutation is responsible for the ultra-low anatabine trait. See Table 6.

TABLE 6

Stability of mutant lines

| Line ID | M2 Seed | M3 Seed | M4 Seed | SNP |
|---|---|---|---|---|
| M207 | MS103 Heterozygous | MS4144 Homozygous | MS13379 Homozygous | Homozygous |
| | | | MS13396 Homozygous | Homozygous |
| | | | MS13397 Homozygous | Homozygous |
| | | | MS13398 Homozygous | Homozygous |
| | | | MS13399 Homozygous | Homozygous |
| | | | MS13400 Heterozygous | Heterozygous |
| | | | MS13401 Homozygous | Homozygous |
| | | | MS13473 Homozygous | Homozygous |
| | | | MS13537 Homozygous | Homozygous |
| | | | MS13374 Homozygous | Homozygous |
| | | MS12469 Heterozygous | MS13391 Homozygous | Homozygous |
| | | | MS13392 Homozygous | Homozygous |
| | | | MS13393 Homozygous | Homozygous |
| M544 | MS445 Heterozygous | MS4360 Homozygous | MS13474 Homozygous | Homozygous |
| | | | MS13540 Homozygous | Homozygous |
| | | MS12471 Heterozygous | MS13370 Homozygous | Homozygous |
| | | | MS13371 Homozygous | Homozygous |
| | | | MS13389 Homozygous | Homozygous |

Figure 6:
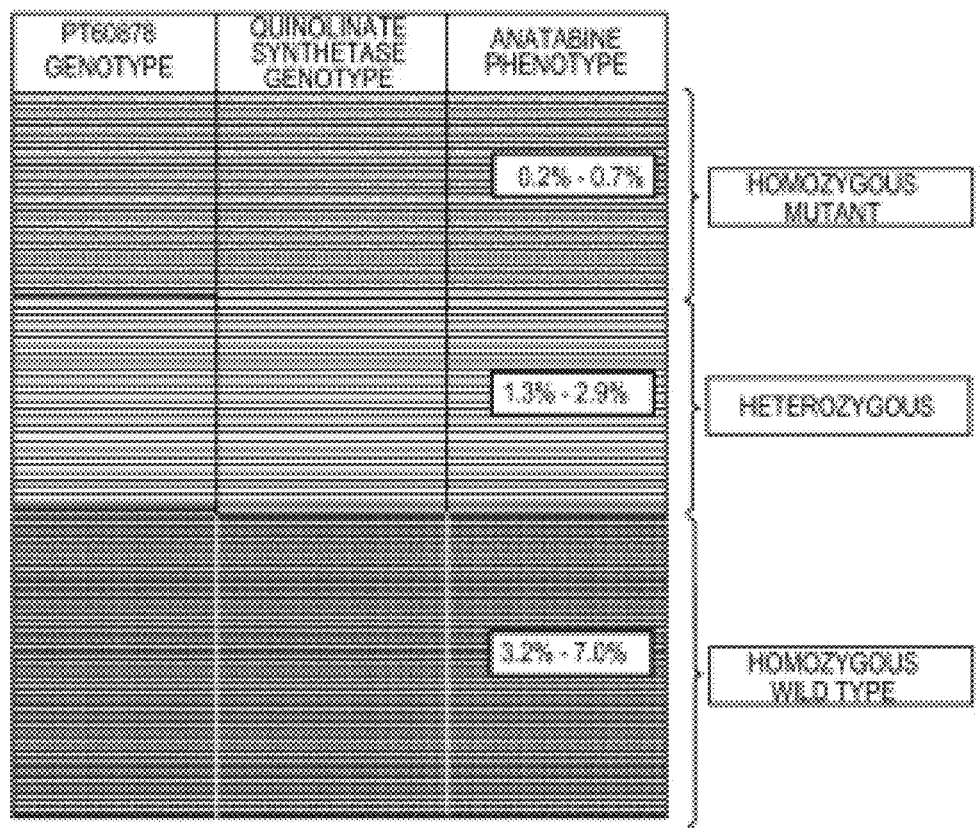
FIG. 6 is an image showing co-segregation of the mutants with anatabine.
Figure 8:
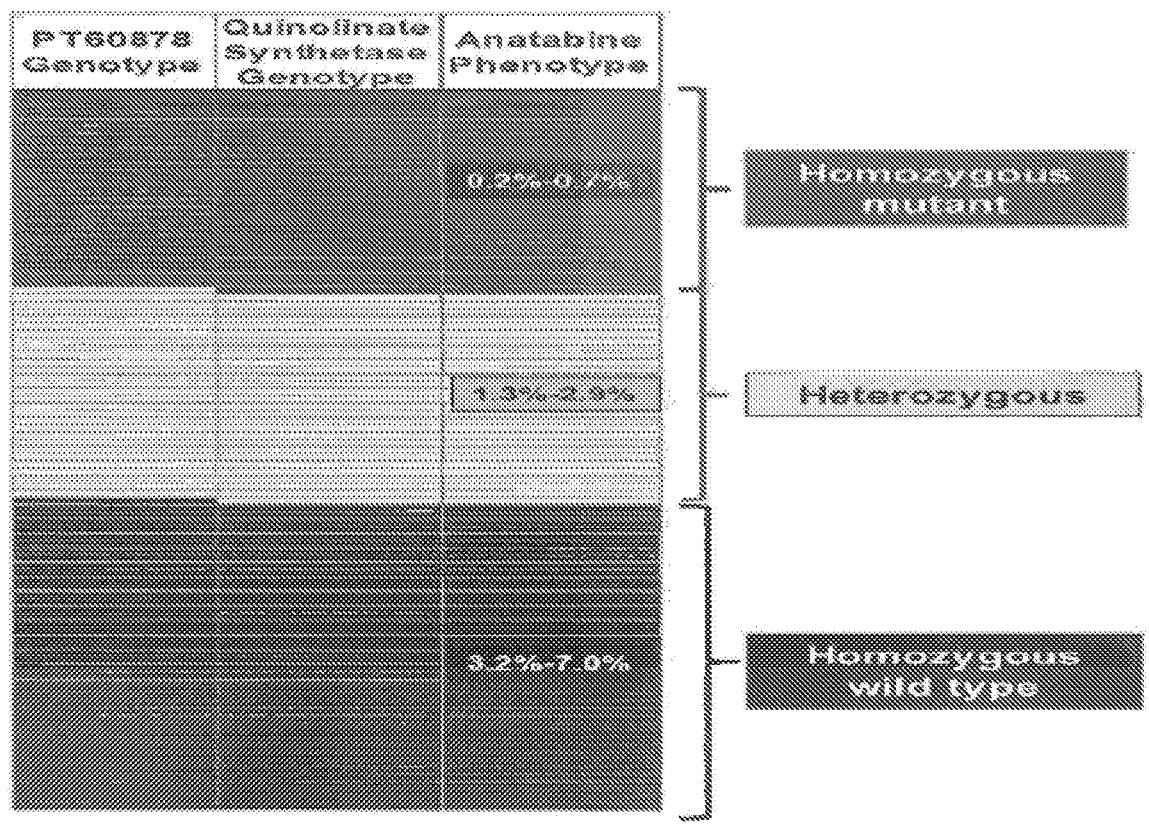

In order to verify the linkage between the low anatabine phenotype and the QS SNP genotype, a mapping population was tested for both anatabine level and SNPs. The mapping population was generated previously by crossing mutant line M207 and wild type Red Russian. FIG. 6 shows the linkage between the anatabine trait, the PT60808 genetic marker, which is the genetic marker that is the most tightly linked to the trait, and the QS mutation. From 115 F2 plants tested, the QS mutation co-segregated with the low anatabine trait.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

```
                           SEQUENCE LISTING

Sequence total quantity: 56
SEQ ID NO: 1             moltype = DNA  length = 211
FEATURE                  Location/Qualifiers
source                   1..211
                         mol_type = unassigned DNA
                         organism = Nicotiana tabacum
SEQUENCE: 1
agtggcggag gtaggaattt caccaagaga attcaaaaaa ataaaagtat acatgcaaag    60
aagcaaacgt gattcatcac ctaatatata tatatatata tatatatata tatatatata   120
tatatatata tatatatata tatatacata tacataaaaa taaaatttga ctttatatac   180
atagtgtaat ttcccggcta cctcactctt a                                  211

SEQ ID NO: 2             moltype = DNA  length = 110
FEATURE                  Location/Qualifiers
source                   1..110
                         mol_type = unassigned DNA
                         organism = Nicotiana tabacum
SEQUENCE: 2
ccctttgcca ctttacaaga attttccctc atgtcgaggg gattcaacag cttttatata    60
tatatatata tatataaagg aaaaaagtag ttgttatcct atttgcacaa               110

SEQ ID NO: 3             moltype = DNA  length = 197
FEATURE                  Location/Qualifiers
source                   1..197
                         mol_type = unassigned DNA
                         organism = Nicotiana tabacum
SEQUENCE: 3
agctccattt gtacttccgc gagcgaggtt ccagacagcc tatttaataa tatatatata    60
tatatatata tatattcaca aatattgtgt atatactaca tacacacaca tatataaagt   120
gtgcatagtg taaacaatag ctcacttatt cacataagac ttaagtttgt ataatcatct   180
tggaacgtct gttagaa                                                  197

SEQ ID NO: 4             moltype = DNA  length = 259
FEATURE                  Location/Qualifiers
source                   1..259
                         mol_type = unassigned DNA
                         organism = Nicotiana tabacum
SEQUENCE: 4
cacaagaccc ttcttggtgc tgtagaaatt gaaagaaatg caaaggcttt ttttctactc    60
tatcctgtat ttcaatgttt ggtgtgatta agctattatg cagaattttg tatagcaagg   120
aaccatatat atatatatat atatatatat atatatatat actagacagg gttgctgccc   180
aaaatattag gcgtgaagcc tgtcttggtg gcaatatcaa tagtgctccg cccaaaatat   240
taggcgtgaa gcctgtctt                                                259

SEQ ID NO: 5             moltype = DNA  length = 199
FEATURE                  Location/Qualifiers
source                   1..199
                         mol_type = unassigned DNA
                         organism = Nicotiana tabacum
SEQUENCE: 5
cagagattac acccattgtg cttcttttta aaggagtaaa gtgggaaaaa atcaccaaat    60
acttgaataa agacagaaa taacccctct ctctctctct ctctcacaca cactcctttt   120
tcggcattta tattatagag cacacagaca atagatctat gggtgagaaa gatactatta   180
ctacctacat tgacggcgg                                                199

SEQ ID NO: 6             moltype = DNA  length = 132
```

| FEATURE | Location/Qualifiers |
|---|---|
| source | 1..132 |
| | mol_type = unassigned DNA |
| | organism = Nicotiana tabacum |

SEQUENCE: 6
```
tgtctcaact tcttgtcaat tgctaatcac tcttttttatg gaattgacat gctacatata    60
tatatatata tatatatata ttacttttct tagcaaatat atttataagt atcgcaggat   120
gacataataa gg                                                       132
```

| SEQ ID NO: 7 | moltype = DNA  length = 2166 |
|---|---|
| FEATURE | Location/Qualifiers |
| source | 1..2166 |
| | mol_type = unassigned DNA |
| | organism = Nicotiana tabacum |

SEQUENCE: 7
```
atggatgccg caaatttagt catgaaatct tccttgtttt cgaaatcccc atgtcccctt    60
tttagttcta aactcattcc tagagcacca ccctctgtct ttactctgcc ttctaccttt   120
agacccctcg ttaaatgcat acaagcttca ttcccaccaa accctgattc caaaaaaccc   180
tcaaacaatt caacctttac gtgttcagct gtgacttcct tcccttctca acaatctcag   240
cctcacgcgc cttccgatgc caagctccaa ctcctgatct ctgaattcca gtccctcgtc   300
gaaccaatgg accgcgtgaa acgcctcttg cactactcca cactcctccc tccaatggac   360
gcgtccttca aaaccctga gaatcgcgta ccggggttgca ctacacaggt atggctgaac   420
gtgagtttcg atgaggctga aacaggatg aaatttttgg cggacagtga ctcggaaata   480
actaaagggt tttgcgcgtg tttggttcg ctgctggacg gggctactcc cgatgaggtg   540
ctggcgttga aaacggagga cttgaatgct tgaatgttg cggggttgaa cgggaaagga   600
tcggcatcta gggcgaatac gtggcataat gtgttggtca gcatgcagaa aaggacaagg   660
gccttagttg cggagcgtga aggcaggccg cgcggcgagc tctttccatc tctagtaatc   720
acagctgatg gtatccaacc ccaaggcagc tacgctgaag cccaggcaag gttcctgttt   780
cctgatgaat caagggtcca aaaacttgcc aatttgctaa aggagaagaa ataggagtt   840
gttgctcatt tctacatgga ccctgaggtg caaggtgttc taactgcagc gcagaagctt   900
tggccccata tacatatatc tgattctta gtcatggctg ataaagctgt cagtatggca   960
aaagctggat gtgaatatat atctgtattg ggtgtagatt tcatgtcaga aatgtgcga   1020
gccattcttg atctagctgg attcccagag gttggagttt atcggatgtc ggacgaacgc   1080
attggttgtt ctttggctga tgctgcagcc agcccagcat acttgatta tcttaaaaca   1140
gcttcaactt cttcctccatc tctgcatgtt gtgtacataa atacttcact ggagacaaaa   1200
gcatattctc atgagcttgt tccgactata acatgtactt cctctaatgt tgtgcaaact   1260
attctgcagg catttgctga gtacctgac ttggaagtgt tgtatggtcc tgataccttac   1320
atgggttcaa acattgcgga attgttcacc cagatgtcca cgatgactga tgaagaaatt   1380
tctgcgatac atccttttgca caacagaatc tccattaaat ctttgcttcc tcgactgcat   1440
tattttcagg atgggacatg tattgttcat cacctctttg gtcatgaagt tgtggagaag   1500
ataaatgaaa tgtatgggga tgcattcctt actgcacact ttgaagttcc tggtgaaatg   1560
ttttccctgg caatggaagc gaagaaaagg gcatgggag tagtaggttc tacctcgaac   1620
atactcgact ttatcaaaga aagggtagaa gagtccttga atagaaacgt agatgaacat   1680
cttcagttg ttttgggaac ggaatcagga atgattacgg caatagttgc agcagtcggt   1740
aaattactag gttctgctga ctcctcttcc ggtggagcaa aagtaagtgt tgagattgtc   1800
tttcctgtct cgtcagaatc agtgacaaga acatctacgg gttcgcctct ggaccaaaat   1860
aaggtcaata ttatacctgg agttgcaagt ggagagggt gttctctaca tggtggatgt   1920
gcctcctgtc catatatgaa gatgaactct cttagctcgt tgctaaagt ttgccagagc   1980
ttgccccatg gcaaagccga actttcagct tatgaggcag gacgattcag tttgcgaacc   2040
cccaaggga acaaattgc ggatgttggt tgtgagccgg ttctgcacat gagacacttt   2100
caggcaacaa agagattacc cagagcagcta atcaatcaaa tacttcaacg atcaagctct   2160
gcttaa                                                            2166
```

| SEQ ID NO: 8 | moltype = AA  length = 721 |
|---|---|
| FEATURE | Location/Qualifiers |
| source | 1..721 |
| | mol_type = protein |
| | organism = Nicotiana tabacum |

SEQUENCE: 8
```
MDAANLVMKS SLFSKSPCPL FSSKLIPRAP PSVFTLPSTF RPLVKCIQAS FPPNPDSKKP    60
SNNSTFTCSA VTSFPSQQSQ PHAPSDAKLQ LLISEFQSLV EPMDRVKRLL HYSTLLPPMD   120
ASFKTPENRV PGCTTQVWLN VSFDEAENRM KFLADSDSEI TKGFCACLVS LLDGATPDEV   180
LALKTEDLNA LNVAGLNGKG SASRANTWHN VLVSMQKRTR ALVAEREGRP RGELFPSLVI   240
TADGIQPQGS YAEAQARFLF PDESRVQKLA NLLKEKKIGV VAHFYMDPEV QGVLTAAQKL   300
WPHIHISDSL VMADKAVSMA KAGCEYISVL GVDFMSENVR AILDLAGFPE VGVYRMSDER   360
IGCSLADAAA SPAYLDYLKT ASTSSPSLHV VYINTSLETK AYSHELVPTI TCSSNVVQT    420
ILQAFAEVPD LEVLYGPDTY MGSNIAELFT QMSTMTDEEI SAIHPLHNRI SIKSLLPRLH   480
YFQDGTCIVH HLFGHEVVEK INEMYGDAPL TAHFEVPGEM FSLAMEAKKR GMGVVGSTSN   540
ILDFIKERVE ESLNRNVDEH LQFVLGTESG MITAIVAAVG KLLGSADSSS GGAKVSVEIV   600
FPVSSESVTR TSTGSPLDQN KVNIIPGVAS GEGCSLHGGC ASCPYMKMNS LSSLLKVCQS   660
LPHGKAELSA YEAGRFSLRT PKGKQIADVG CEPVLHMRHF QATKRLPEQL INQILQRSSS   720
A                                                                   721
```

| SEQ ID NO: 9 | moltype = DNA  length = 20 |
|---|---|
| FEATURE | Location/Qualifiers |
| misc_feature | 1..20 |
| | note = synthetic oligonucleotide |
| source | 1..20 |
| | mol_type = other DNA |

```
                            -continued organism = synthetic construct
SEQUENCE: 9
agtggcggag gtaggaattt                                               20

SEQ ID NO: 10               moltype = DNA   length = 20
FEATURE                     Location/Qualifiers
misc_feature                1..20
                            note = synthetic oligonucleotide
source                      1..20
                            mol_type = other DNA
                            organism = synthetic construct
SEQUENCE: 10
taagagtgag gtagccggga                                               20

SEQ ID NO: 11               moltype = DNA   length = 21
FEATURE                     Location/Qualifiers
misc_feature                1..21
                            note = synthetic oligonucleotide
source                      1..21
                            mol_type = other DNA
                            organism = synthetic construct
SEQUENCE: 11
ccctttgcca ctttacaaga a                                             21

SEQ ID NO: 12               moltype = DNA   length = 27
FEATURE                     Location/Qualifiers
misc_feature                1..27
                            note = synthetic oligonucleotide
source                      1..27
                            mol_type = other DNA
                            organism = synthetic construct
SEQUENCE: 12
ttgtgcaaat aggataacaa ctacttt                                       27

SEQ ID NO: 13               moltype = DNA   length = 20
FEATURE                     Location/Qualifiers
misc_feature                1..20
                            note = synthetic oligonucleotide
source                      1..20
                            mol_type = other DNA
                            organism = synthetic construct
SEQUENCE: 13
agctccattt gtacttccgc                                               20

SEQ ID NO: 14               moltype = DNA   length = 23
FEATURE                     Location/Qualifiers
misc_feature                1..23
                            note = synthetic oligonucleotide
source                      1..23
                            mol_type = other DNA
                            organism = synthetic construct
SEQUENCE: 14
ttctaacaga cgttccaaga tga                                           23

SEQ ID NO: 15               moltype = DNA   length = 20
FEATURE                     Location/Qualifiers
misc_feature                1..20
                            note = synthetic oligonucleotide
source                      1..20
                            mol_type = other DNA
                            organism = synthetic construct
SEQUENCE: 15
cacaagaccc ttcttggtgc                                               20

SEQ ID NO: 16               moltype = DNA   length = 20
FEATURE                     Location/Qualifiers
misc_feature                1..20
                            note = synthetic oligonucleotide
source                      1..20
                            mol_type = other DNA
                            organism = synthetic construct
SEQUENCE: 16
acgtggagtg gagaaaccag                                               20

SEQ ID NO: 17               moltype = DNA   length = 22
FEATURE                     Location/Qualifiers
misc_feature                1..22
                            note = synthetic oligonucleotide
source                      1..22
```

```
                    mol_type = other DNA
                    organism = synthetic construct
SEQUENCE: 17
cagagattac acccattgtg ct                                              22

SEQ ID NO: 18           moltype = DNA  length = 20
FEATURE                 Location/Qualifiers
misc_feature            1..20
                    note = synthetic oligonucleotide
source                  1..20
                    mol_type = other DNA
                    organism = synthetic construct
SEQUENCE: 18
ccgccgtcaa tgtaggtagt                                                 20

SEQ ID NO: 19           moltype = DNA  length = 24
FEATURE                 Location/Qualifiers
misc_feature            1..24
                    note = synthetic oligonucleotide
source                  1..24
                    mol_type = other DNA
                    organism = synthetic construct
SEQUENCE: 19
tgtctcaact tcttgtcaat tgct                                            24

SEQ ID NO: 20           moltype = DNA  length = 21
FEATURE                 Location/Qualifiers
misc_feature            1..21
                    note = synthetic oligonucleotide
source                  1..21
                    mol_type = other DNA
                    organism = synthetic construct
SEQUENCE: 20
ccttattatg tcatcctgcg a                                               21

SEQ ID NO: 21           moltype = DNA  length = 21
FEATURE                 Location/Qualifiers
misc_feature            1..21
                    note = synthetic oligonucleotide
source                  1..21
                    mol_type = other DNA
                    organism = synthetic construct
SEQUENCE: 21
atctttgctt cctcgactcc a                                               21

SEQ ID NO: 22           moltype = DNA  length = 21
FEATURE                 Location/Qualifiers
misc_feature            1..21
                    note = synthetic oligonucleotide
source                  1..21
                    mol_type = other DNA
                    organism = synthetic construct
SEQUENCE: 22
agttaagcgg agcttgatcg t                                               21

SEQ ID NO: 23           moltype = DNA  length = 18
FEATURE                 Location/Qualifiers
misc_feature            1..18
                    note = synthetic oligonucleotide
source                  1..18
                    mol_type = other DNA
                    organism = synthetic construct
SEQUENCE: 23
atgaggtgct ggcgttga                                                   18

SEQ ID NO: 24           moltype = DNA  length = 18
FEATURE                 Location/Qualifiers
misc_feature            1..18
                    note = synthetic oligonucleotide
source                  1..18
                    mol_type = other DNA
                    organism = synthetic construct
SEQUENCE: 24
ttcagcgtag ctgccttg                                                   18

SEQ ID NO: 25           moltype = DNA  length = 18
FEATURE                 Location/Qualifiers
misc_feature            1..18
                    note = synthetic oligonucleotide
```

```
source                   1..18
                         mol_type = other DNA
                         organism = synthetic construct
SEQUENCE: 25
ggagtttatc ggatgtcg                                               18

SEQ ID NO: 26            moltype = DNA   length = 20
FEATURE                  Location/Qualifiers
misc_feature             1..20
                         note = synthetic oligonucleotide
source                   1..20
                         mol_type = other DNA
                         organism = synthetic construct
SEQUENCE: 26
tgtgcagtaa ggaatgcatc                                             20

SEQ ID NO: 27            moltype = DNA   length = 20
FEATURE                  Location/Qualifiers
misc_feature             1..20
                         note = synthetic oligonucleotide
source                   1..20
                         mol_type = other DNA
                         organism = synthetic construct
SEQUENCE: 27
gttgtgagcc ggttctgcac                                             20

SEQ ID NO: 28            moltype = DNA   length = 25
FEATURE                  Location/Qualifiers
misc_feature             1..25
                         note = synthetic oligonucleotide
source                   1..25
                         mol_type = other DNA
                         organism = synthetic construct
SEQUENCE: 28
atggacgccg caaatttagt catga                                       25

SEQ ID NO: 29            moltype = DNA   length = 28
FEATURE                  Location/Qualifiers
misc_feature             1..28
                         note = synthetic oligonucleotide
source                   1..28
                         mol_type = other DNA
                         organism = synthetic construct
SEQUENCE: 29
agtgactcgg aaataactaa agggtttt                                    28

SEQ ID NO: 30            moltype = DNA   length = 29
FEATURE                  Location/Qualifiers
misc_feature             1..29
                         note = synthetic oligonucleotide
source                   1..29
                         mol_type = other DNA
                         organism = synthetic construct
SEQUENCE: 30
aagtattagt cacaacatgc agagatgag                                   29

SEQ ID NO: 31            moltype = DNA   length = 27
FEATURE                  Location/Qualifiers
misc_feature             1..27
                         note = synthetic oligonucleotide
source                   1..27
                         mol_type = other DNA
                         organism = synthetic construct
SEQUENCE: 31
gagctctttc catctctagt aatcaca                                     27

SEQ ID NO: 32            moltype = DNA   length = 27
FEATURE                  Location/Qualifiers
misc_feature             1..27
                         note = synthetic oligonucleotide
source                   1..27
                         mol_type = other DNA
                         organism = synthetic construct
SEQUENCE: 32
atgtaggtat caggaccata caacact                                     27

SEQ ID NO: 33            moltype = DNA   length = 21
FEATURE                  Location/Qualifiers
misc_feature             1..21
```

```
                           note = synthetic oligonucleotide
source                     1..21
                           mol_type = other DNA
                           organism = synthetic construct
SEQUENCE: 33
gttcgaggta gaacctacta g                                             21

SEQ ID NO: 34              moltype = AA  length = 41
FEATURE                    Location/Qualifiers
source                     1..41
                           mol_type = protein
                           organism = Nicotiana tabacum
SEQUENCE: 34
GTCIVHHLFG HEVVENINEM YGDAFLTAHF EVPGEMFSLA M                        41

SEQ ID NO: 35              moltype = AA  length = 41
FEATURE                    Location/Qualifiers
source                     1..41
                           mol_type = protein
                           organism = Nicotiana tabacum
SEQUENCE: 35
GTYIVHHLFG HEVVENINEM YGDAFLTAHF EVPGEMFSLA M                        41

SEQ ID NO: 36              moltype = AA  length = 41
FEATURE                    Location/Qualifiers
source                     1..41
                           mol_type = protein
                           organism = Nicotiana tabacum
SEQUENCE: 36
GTCIVHHLFG HEVVENINEM YGDAFLTAHF EIPGEMFSLA M                        41

SEQ ID NO: 37              moltype = AA  length = 41
FEATURE                    Location/Qualifiers
source                     1..41
                           mol_type = protein
                           organism = Nicotiana tabacum
SEQUENCE: 37
GTCIVHHIFG GEVTELVAAG YGDAYLAAHF EVPGEMFRLA M                        41

SEQ ID NO: 38              moltype = AA  length = 41
FEATURE                    Location/Qualifiers
source                     1..41
                           mol_type = protein
                           organism = Nicotiana tabacum
SEQUENCE: 38
GTCIVHHIFG GEVTELVAAG YGDAYLAAHF EVPGEMFRLA M                        41

SEQ ID NO: 39              moltype = AA  length = 41
FEATURE                    Location/Qualifiers
source                     1..41
                           mol_type = protein
                           organism = Nicotiana tabacum
SEQUENCE: 39
GNCIVHHMFG DDVVERVRSN HADAFHTAHL EVPGEMFRLA M                        41

SEQ ID NO: 40              moltype = AA  length = 41
FEATURE                    Location/Qualifiers
source                     1..41
                           mol_type = protein
                           organism = Nicotiana tabacum
SEQUENCE: 40
GTCIVHHLFG HEVVERTKYM YCDAFITAHL EVPGEMFSLA M                        41

SEQ ID NO: 41              moltype = AA  length = 41
FEATURE                    Location/Qualifiers
source                     1..41
                           mol_type = protein
                           organism = Nicotiana tabacum
SEQUENCE: 41
GTCIVHHLFG HEVVEKTNEM YCDAFITAHL EVPGEMFSLA M                        41

SEQ ID NO: 42              moltype = AA  length = 41
FEATURE                    Location/Qualifiers
source                     1..41
                           mol_type = protein
                           organism = Nicotiana tabacum
SEQUENCE: 42
GSCIVHDMFG HDVVSRVREG YGDAYLTAHF EVPGEMFTLA M                        41
```

-continued

```
SEQ ID NO: 43            moltype = AA   length = 41
FEATURE                  Location/Qualifiers
source                   1..41
                         mol_type = protein
                         organism = Nicotiana tabacum
SEQUENCE: 43
GSCIVHDMFG HDVVSRVREG YGDAYLTAHF EVPGEMFTLA M                      41

SEQ ID NO: 44            moltype = AA   length = 41
FEATURE                  Location/Qualifiers
source                   1..41
                         mol_type = protein
                         organism = Nicotiana tabacum
SEQUENCE: 44
GTCIVHHIFG GEVAELVRRA YGDAYLAAHF EVPGEMFGLA M                      41

SEQ ID NO: 45            moltype = DNA   length = 30
FEATURE                  Location/Qualifiers
source                   1..30
                         mol_type = unassigned DNA
                         organism = Nicotiana tabacum
SEQUENCE: 45
aggatgggac atatattgtt catcacctct                                   30

SEQ ID NO: 46            moltype = AA   length = 9
FEATURE                  Location/Qualifiers
source                   1..9
                         mol_type = protein
                         organism = Nicotiana tabacum
SEQUENCE: 46
DGTYIVHHL                                                           9

SEQ ID NO: 47            moltype = DNA   length = 30
FEATURE                  Location/Qualifiers
source                   1..30
                         mol_type = unassigned DNA
                         organism = Nicotiana tabacum
SEQUENCE: 47
aggatgggac atgtattgtt catcacctct                                   30

SEQ ID NO: 48            moltype = AA   length = 9
FEATURE                  Location/Qualifiers
source                   1..9
                         mol_type = protein
                         organism = Nicotiana tabacum
SEQUENCE: 48
DGTCIVHHL                                                           9

SEQ ID NO: 49            moltype = DNA   length = 30
FEATURE                  Location/Qualifiers
source                   1..30
                         mol_type = unassigned DNA
                         organism = Nicotiana tabacum
SEQUENCE: 49
aggatgggac atgtattgtt catcacctct                                   30

SEQ ID NO: 50            moltype = AA   length = 9
FEATURE                  Location/Qualifiers
source                   1..9
                         mol_type = protein
                         organism = Nicotiana tabacum
SEQUENCE: 50
DGTCIVHHL                                                           9

SEQ ID NO: 51            moltype = DNA   length = 26
FEATURE                  Location/Qualifiers
source                   1..26
                         mol_type = unassigned DNA
                         organism = Nicotiana tabacum
SEQUENCE: 51
cacactttga agttcctggt gaaatg                                       26

SEQ ID NO: 52            moltype = AA   length = 8
FEATURE                  Location/Qualifiers
source                   1..8
                         mol_type = protein
                         organism = Nicotiana tabacum
SEQUENCE: 52
HFEVPGEM                                                            8
```

```
SEQ ID NO: 53          moltype = DNA  length = 26
FEATURE                Location/Qualifiers
source                 1..26
                       mol_type = unassigned DNA
                       organism = Nicotiana tabacum
SEQUENCE: 53
cacactttga aattcctggt gaaatg                                            26

SEQ ID NO: 54          moltype = AA  length = 8
FEATURE                Location/Qualifiers
source                 1..8
                       mol_type = protein
                       organism = Nicotiana tabacum
SEQUENCE: 54
HFEIPGEM                                                                 8

SEQ ID NO: 55          moltype = DNA  length = 26
FEATURE                Location/Qualifiers
source                 1..26
                       mol_type = unassigned DNA
                       organism = Nicotiana tabacum
SEQUENCE: 55
cacactttga aattcctggt gaaatg                                            26

SEQ ID NO: 56          moltype = AA  length = 8
FEATURE                Location/Qualifiers
source                 1..8
                       mol_type = protein
                       organism = Nicotiana tabacum
SEQUENCE: 56
HFEVPGEM                                                                 8
```

What is claimed is:

1. A tobacco plant having an induced mutation in an endogenous gene, wherein the endogenous gene encodes an amino acid sequence 100% identical to SEQ ID NO: 8, and wherein the tobacco plant having an induced mutation exhibits reduced expression or activity of a quinolinate synthase protein as compared to a control tobacco plant lacking the induced mutation.

2. The tobacco plant of claim 1, wherein leaf from the tobacco plant having an induced mutation comprises a reduced amount of at least one alkaloid as compared to leaf from the control tobacco plant.

3. The tobacco plant of claim 2, wherein the at least one alkaloid is anatabine.

4. The tobacco plant of claim 1, wherein cured leaf from the tobacco plant having an induced mutation exhibits a reduced amount of at least one tobacco-specific nitrosamine (TSNA) as compared to cured leaf from the control tobacco plant.

5. The tobacco plant of claim 4, wherein the at least one TSNA is N'-nitrosoanatabine.

6. The tobacco plant of claim 1, wherein the induced mutation comprises an amino acid substitution at a position corresponding to the cysteine residue at position 487 or the valine residue at position 516 of SEQ ID NO: 8.

7. The tobacco plant of claim 1, wherein the induced mutation results in a cysteine to tyrosine substitution at a position corresponding to the cysteine residue at position 487 of SEQ ID No: 8.

8. The tobacco plant of claim 1, wherein the induced mutation results in a valine to isoleucine substitution at a position corresponding to the valine residue at position 516 of SEQ ID No: 8.

9. The tobacco plant of claim 1, wherein the endogenous gene comprises a nucleotide sequence at least 95% identical to SEQ ID NO: 7.

10. The tobacco plant of claim 1, wherein the tobacco plant is a Burley type, a dark type, a flue-cured type, a Maryland type, or an Oriental type.

11. The tobacco plant of claim 1, wherein the tobacco plant is from a tobacco variety selected from the group consisting of FC401, Red Russian, BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, and VA359.

12. A cured tobacco leaf from the tobacco plant of claim 1, wherein the cured tobacco leaf comprises the induced mutation.

13. The cured tobacco leaf of claim 12, wherein the cured tobacco leaf comprises an anatabine percentage of less than 0.5%.

14. The cured tobacco leaf of claim 12, wherein the cured tobacco leaf is selected from the group consisting of an air cured tobacco leaf, a fire cured tobacco leaf, a flue cured tobacco leaf, and a sun cured tobacco leaf.

15. A tobacco product comprising the cured tobacco leaf of claim 12.

16. The tobacco product of claim 15, wherein the tobacco product is selected from the group consisting of tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, cut tobacco, electronic cigarettes, electronic cigars, electronic cigarillos, and e-vapor devices.

17. The tobacco product of claim 15, wherein the tobacco product is a smokeless tobacco product.

18. The tobacco product of claim 17, wherein the smokeless tobacco product is selected from the group consisting of chewing tobacco, snus, pouches, films, and tablets.

\* \* \* \* \*